United States Patent [19]

Koden et al.

[11] Patent Number: 5,437,814
[45] Date of Patent: Aug. 1, 1995

[54] FERROELECTRIC LIQUID CRYSTAL MIXTURE AND LIQUID CRYSTAL DEVICE USING THE SAME

[75] Inventors: Mitsuhiro Koden, Nara; Takashi Kaneko; Hitoshi Takeda, both of Tenri; Keizou Itoh; Mitsunori Takeda, both of Kashima, all of Japan

[73] Assignees: Sharp Kabushiki Kaisha; Kashima Oil Co., Ltd., both of Japan

[21] Appl. No.: 233,808

[22] Filed: Apr. 26, 1994

[30] Foreign Application Priority Data

Apr. 26, 1993 [JP] Japan .................................. 5-99868
Jun. 15, 1993 [JP] Japan .................................. 5-143708

[51] Int. Cl.$^6$ .......................... C09K 19/34; G02F 1/13
[52] U.S. Cl. ........................... 252/299.61; 252/299.01; 359/104
[58] Field of Search ................. 252/299.01, 299.61, 252/299.64, 299.65, 299.66, 299.67; 359/103, 104

[56] References Cited

U.S. PATENT DOCUMENTS 5,296,616  3/1994  Namekawa et al. ............. 549/417

FOREIGN PATENT DOCUMENTS

| | | |
|---|---|---|
| 0396410A2 | 11/1990 | European Pat. Off. |
| 0457105A1 | 11/1991 | European Pat. Off. |
| 0594861A1 | 5/1994 | European Pat. Off. |
| 62-240378 | 10/1987 | Japan |
| 2-004724 | 1/1990 | Japan |
| 2-004725 | 1/1990 | Japan |
| 2-502914 | 9/1990 | Japan |
| 2-503430 | 10/1990 | Japan |
| 2-503431 | 10/1990 | Japan |
| 2-503436 | 10/1990 | Japan |
| 2-503441 | 10/1990 | Japan |
| 2-503443 | 10/1990 | Japan |
| 2-503568 | 10/1990 | Japan |
| 2-279649 | 11/1990 | Japan |
| 2-289529 | 11/1990 | Japan |
| 2-504520 | 12/1990 | Japan |
| 9202925 | 2/1992 | WIPO |
| WO93/13088 | 7/1993 | WIPO |
| 9313088 | 7/1993 | WIPO |

OTHER PUBLICATIONS

N. A. Clark, et al., *Appl. Phys. Lett.* 36 (11), Jun. 1, 1980 "Submicrosecond bistable electro-optic switching in liquid crystals".

(List continued on next page.)

*Primary Examiner*—Shean Wu
*Attorney, Agent, or Firm*—David G. Conlin; Peter F. Corless

[57] ABSTRACT

A ferroelectric liquid crystal mixture containing at least one chiral compound, having negative dielectric anisotropy and exhibiting a chiral smectic C phase includes at least one compound selected from the group consisting of a compound represented by the following general Formula I and a compound represented by the following general Formula II:

$$R^1-X^1-A-Z-B-Y-\underset{\underset{CF_3}{O}}{\bigcirc}-X^2-R^2 \quad (I)$$

$$R^1-X^1-A-Z-B-Y-\underset{\underset{CF_3}{O}}{\bigcirc}-X^2-R^2 \quad (II)$$

where $R^1$ and $R^2$ are the same or different straight-chain or branched chain alkyl groups having 1 to 15 carbon atoms; $X^1$ is a single bond, —O—, —COO—, or —OCO—; $X^2$ is —O— or —OCO—; Y is —COO— or —CH$_2$O—; A and B are independently a group including a six membered ring which can be substituted by halogen, a cyano group, a lower alkoxy group, or a fluorine-containing alkyl group; and Z is a single bond, —COO—, or —OCO—.

13 Claims, 20 Drawing Sheets

OTHER PUBLICATIONS

T. Uemura, et al., Proceedings of the SID, vol. 28/2, 1987, "Alignment of chiral smectic-C liquid crystals by oblique evaporation Method".

N. Yamamoto, et al., *Japanese Journal of Applied Physics*, vol. 28, No. 3, pp. 524–529, Mar. 1989 "Ferroelectric Liquid Crystal Display with High Contrast Ratio".

Y. Sato, et al., *Japanese Journal of Applied Physics*, vol. 28, No. 3, pp. L 483–L 486, Mar. 1989 "High Quality Ferroelectic Liquid Crystal Display with Quasi-Bookshelf Layer Structure".

H. Rieger, et al., *SID 91 Digest*, pp. 396–399, 1991 "FLCD Showing High Contrast and High Luminance".

A. Mochizuki, et al., *Ferroelectrics*, vol. 122, pp. 37–51, 1991 "A High Contrast and High Transmittance Multiplexing SSFLC Display Utilizing Naphthalene Base Liquid Crystal Materials".

M. Koden, et al. *Future Liquid Crystal Display and its Materials: Ferroelectric Liquid Crystal and Anti–ferroelectric Liquid Crystal*, pp. 114–125, 1992 "Method for Driving Ferroelectric Liquid Crystal Display and Orientation State".

P. W. H. Surgay et al., *Ferroelectrics*, vol. 122, pp. 63–79, 1991 "The Joers/Alvey" Ferroelectric Multiplexing Scheme.

P. W. Ross, et al., *SID 92 Digest*, pp. 217–220, 1992 "Color Digital Ferroelectric LCDs for Laptop Applications".

G. W. Gray et al., *Mol. Cryst. Liq. Cryst.*, vol 204, pp. 43–64 1991 "The Synthesis of Several Lateral . . . ".

M. Koden, et al., *Japanese Journal of Applied Physics*, vol. 30, No. 10B, pp.L 1823–L 1825 Oct., 1991. "The States of Surface–Stabilized Ferroelectric Liquid Crystal with High-Pretilt Aligning Film".

T. Yamazaki, et al., *J. Chem. Soc., Chem. Commun.*, pp. 55–57, 1992 "Chiral Trifluoromethylated . . . ".

M. Takeda, et al., *The 18th Symposium on Liquid Crystals*, Niigata, Japan, pp. 338–339, 1992 "Ferroelectric Liquid Crystal . . . " (with partial English translation).

Fig.3
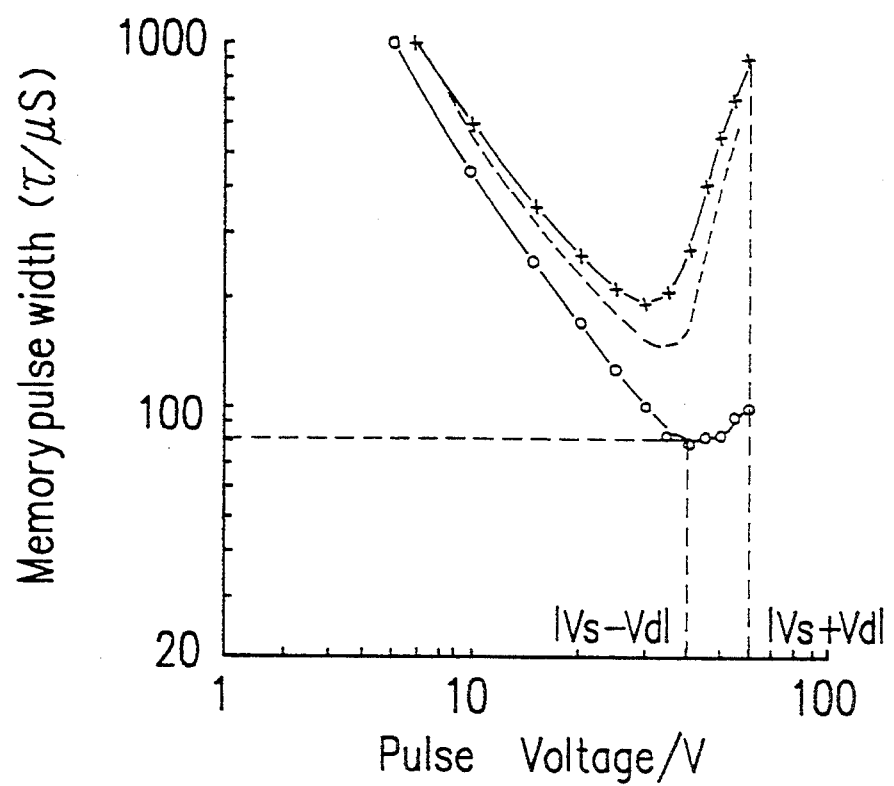
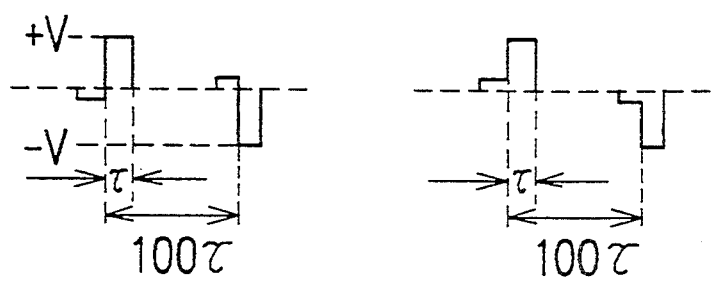

Model of SSFLC having a chevron structure

Fig.7 AC stabilizing method

FERROELECTRIC LIQUID CRYSTAL MIXTURE AND LIQUID CRYSTAL DEVICE USING THE SAME

BACKGROUND OF THE INVENTION

1. Field of the Invention

The present invention relates to a ferroelectric liquid crystal mixture and a liquid crystal device using the same.

2. Description of the Related Art

Liquid crystal display devices which have been most widely used in recent years employ a nematic phase of liquid crystal. In twisted nematic (TN) liquid crystal display devices, it is difficult to realize a display with a large capacity, e.g., 2000×2000 lines, since contrast decreases with the increase in the number of lines. In order to improve the TN liquid crystal display devices, supertwisted nematic (STN) liquid crystal display devices and double layer supertwisted nematic (DSTN) liquid crystal display devices have been developed. However, in these devices, contrast decreases and response time becomes longer with the increase in the number of lines; therefore, display capacity is now limited to about 800×1024 lines.

Active matrix type liquid crystal display devices have been developed to realize a display with a large capacity, e.g., 1000×1000 lines. These devices also have disadvantages such as many steps for prolonged production, a decrease in yield, and high production cost.

In recent years, in addition to liquid crystal display devices employing a nematic phase, those employing a smectic phase have been extensively studied. In particular, a ferroelectric liquid crystal display device has been considered to be promising (N. A. Clark et al., Appl. Phys. Lett., 36, 899 (1980)). The ferroelectric liquid crystal display device employs a memory property of a chiral smectic C phase, a chiral smectic I phase, and the like. Because of this, the ferroelectric liquid crystal display device enables a display with a large capacity accompanied by the decrease in response time. In addition, since the ferroelectric liquid crystal display device does not require an active element such as a thin film transistor, production cost is not likely to increase. Furthermore, the ferroelectric liquid crystal display device has an advantage of a large viewing angle, so that it has been promising as a display device with a large capacity, e.g., 2000×2000 lines.

There are various problems to be solved for putting the ferroelectric liquid crystal display device into practical use. Among them, it is most important to find a means for realizing high contrast in a simple matrix drive. Regarding this problem, the following methods have been proposed.

(1) A method for using oblique vacuum evaporation
(2) A method for using a high pretilt alignment film
(3) A method for processing using an AC electric field
(4) A method for using a naphthalene compound
(5) A method for using Cl-uniform orientation
(6) A method for using a liquid crystal material having negative dielectric anisotropy A method (1) is proposed in T. Uemura et al., Proc. SID, 175 (1987). This method requires oblique vacuum evaporation, making it difficult to mass-produce a device and to obtain a device with a large area. Another method (2) is proposed in N. Yamamoto et al., Jpn. J. Appl. Phys., 28, 524 (1989). According to the experiences of the inventors, it is not so easy to obtain uniform orientation in a large area using a high pretilt alignment film. Another method (3) is proposed in Y. Sato et al., Jpn. J. Appl. Phys., 28, L483 (1989) and in H. Rieger et al., Proc. SID, 396 (1991). According to this method, an AC electric field with a low frequency and a high voltage is applied to a conventional ferroelectric liquid crystal cell, whereby a chevron structure in a cell is forced to be changed to a quasi-Bookshelf geometry which is nearly ideal. The method (3) has advantages such as a high contrast, a large memory angle and a bright display; however, there are still problems preventing its practical use, such as increased response time and a change in characteristics with time during driving. Another method (4) is proposed in A. Mochizuki et al., Ferroelectrics., 122, 37 (1991). According to this method, a quasi-Bookshelf geometry which is nearly ideal is obtained using a specific naphthalene compound to realize high contrast. However, naphthalene compounds to be used are limited, so that a great amount of difficulty is assumed for realizing a practical ferroelectric liquid crystal display device with a large screen and a large display capacity, using this method. Another method (5) is proposed in Koden et al., Future Liquid Crystal Display and its Materials: Ferroelectric liquid crystal and antiferroelectric liquid crystal, p. 114 (1992) (under the supervision of A. Fukuda). According to this method, high contrast is obtained employing specific orientation such as Cl-uniform obtained in a parallel rubbing liquid crystal cell using an alignment film with a high pretilt angle. Here, "a parallel rubbing cell" refers to a liquid crystal cell fabricated so that rubbing directions of the upper and lower alignment films are identical. In this method, it is difficult to selectively obtain Cl-uniform orientation in a large area.

Another method (6) is proposed in P. W. H. Surguy et al., Ferroelectrics, 122, 63 (1991). This method is a promising method for realizing high contrast. A sample of a ferroelectric liquid crystal display device has already been fabricated using this method (P. W. Ross, Proc. SID, 217 (1992)).

Hereinafter, the method (6) will be described in detail.

A conventional ferroelectric liquid crystal material whose dielectric anisotropy is not negative exhibits a $\tau$-V characteristic shown in FIG. 1A. More specifically, $\tau$ (a memory pulse width, or a pulse width required for memory) monotonously decreases with the increase in voltage. In contrast, a ferroelectric liquid crystal material having negative dielectric anisotropy exhibits a $\tau$-V ($\tau$-$V_{min}$) characteristic having a local minimum value $V_{min}$ shown in FIG. 1B. Surguy et al. have reported a driving method shown in FIG. 2 as a driving method using this characteristic (P. W. H. Surguy et al., Ferroelectrics, 122, 63 (1991)). The principle of this driving method is briefly shown in FIG. 3. According to the principle, when a voltage of $|V_s-V_d|$ is applied, memory states are switched in the ferroelectric liquid crystal display device, and when a voltage of $|V_s+V_d|$ which is higher than $|V_s-V_d|$ and a voltage of $|V_d|$ which is lower than $|V_s-V_d|$ is applied, the memory states are not switched.

A problem of the method (6) lies in the high driving voltage. According to the report of Ross et al. (P. W. Ross, Proc. SID, 217 (1992)), the driving voltage of a sample of a ferroelectric liquid crystal display device is 55 V. The price of an IC driver for driving the ferroelectric liquid crystal display device goes up with the increase in voltage, so that a high driving voltage necessitates the increase in production cost. In order to fabricate a ferroelectric liquid crystal display device at reasonable price, it is required to drive the display with an inexpensive general-purpose IC driver. That is, it is required that a driving voltage is no more than 40 V. A high driving voltage is due to a high local minimum value $V_{min}$ in the $\tau$-$V_{min}$ characteristic. Thus, in order to drive a display with a driving voltage of 40 V or less, a ferroelectric liquid crystal display material exhibiting a local minimum value of about 30 V needs to be developed.

According to Surguy et al. (P. W. H. Surguy et al., Ferroelectrics, 122, 63 (1991)), a local minimum value $V_{min}$ is given by the following equation:

$$V_{min} = E_{min} \cdot d = \frac{P_s}{\sqrt{3 \cdot \epsilon_0 \cdot \Delta\epsilon \cdot \sin^2\theta}} \cdot d$$

where $E_{min}$ is a local minimum value of electric field intensity, d is the cell thickness, Ps is spontaneous polarization, $\Delta\epsilon$ is dielectric anisotropy, and $\theta$ is the tilt angle. As is understood from this equation, in order to obtain a lower local minimum value $V_{min}$, large negative dielectric anisotropy and small spontaneous polarization are required. On the other hand, the response speed of ferroelectric liquid crystal is proportional to spontaneous polarization, so that it is difficult to obtain quick response when spontaneous polarization is decreased.

In general, the ferroelectric liquid crystal mixture is prepared by adding a chiral compound to an achiral liquid crystal mixture exhibiting a smectic C phase. Therefore, it is required that a chiral compound which can cause high response in a small amount is added to an achiral liquid crystal mixture having low viscosity. A chiral compound generally has high viscosity, so that its added amount is preferably small.

In order to obtain a satisfactory ferroelectric liquid crystal device, the following conventional conditions should also be satisfied.

(1) The ferroelectric liquid crystal material exhibits a chiral smectic C phase in a wide range of temperature around room temperature.

(2) The ferroelectric liquid crystal material exhibits a phase sequence of IAC (Isotropic-Smectic A-Smectic C) or INAC (Isotropic-Nematic-Smectic A-Smectic C) so as to obtain satisfactory orientation properties and bistability.

(3) The helical pitch of the chiral nematic phase and the chiral smectic C phase is sufficiently longer than the cell thickness.

(4) The ferroelectric liquid crystal material has satisfactory chemical stability and optical stability.

If required, the tilt angle, refractive index, specific resistance, and the like can be optimized.

SUMMARY OF THE INVENTION

The ferroelectric liquid crystal mixture of this invention, including at least one chiral compound, having negative dielectric anisotropy and exhibiting a chiral smectic C phase, contains at least one compound selected from the group consisting of a compound represented by the following general Formula I:

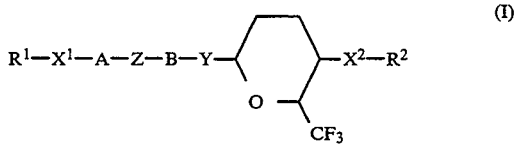

where $R^1$ and $R^2$ are the same or different straight-chain or branched chain alkyl groups having 1 to 15 carbon atoms; $X^1$ is a single bond, —O—, —COO—, or —OCO—; $X^2$ is —O— or —OCO—; Y is —COO— or —CH$_2$O; A and B are independently a group including a six membered ring which can be substituted by halogen, a cyano group, a lower alkoxy group, or a fluorine-containing alkyl group; and Z is a single bond, —COO—, or —OCO—, and a compound represented by the following general Formula II:

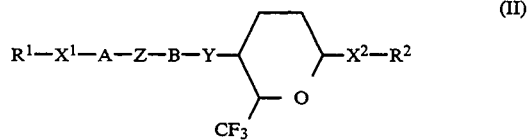

where $R^1$ and $R^2$ are the same or different straight-chain or branched chain alkyl groups having 1 to 15 carbon atoms; $X^1$ is a single bond, —O—, —COO—, or —OCO—; $X^2$ is —O— or —OCO—; Y is —COO— or —CH$_2$O; A and B are independently a group including a six membered ring which can be substituted by halogen, a cyano group, a lower alkoxy group, or a fluorine-containing alkyl group; and Z is a single bond, —COO—, or —OCO—.

In one embodiment of the present invention, the compound represented by Formula I and the compound represented by Formula II are chiral compounds.

In another embodiment of the present invention, the above-mentioned ferroelectric liquid crystal mixture contains the chiral compound represented by Formula I and the chiral compound represented by Formula II.

In another embodiment of the present invention, the above-mentioned ferroelectric liquid crystal mixture exhibits a chiral smectic C phase, a smectic A phase, and a chiral nematic phase.

In another embodiment of the present invention, the above-mentioned ferroelectric liquid crystal mixture contains a compound represented by the following general Formula III:

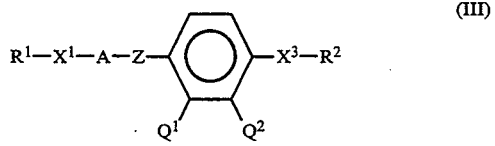

where $R^1$ and $R^2$ are the same or different straight-chain or branched chain alkyl groups having 1 to 15 carbon atoms; $X^1$ is a single bond, —O—, —COO—, or —OCO—; $X^3$ is a single bond, —O—, —COO—, or —OCO—; A is a group including a six membered ring which can be substituted by halogen, a cyano group, a lower alkoxy group, or a fluorine-containing alkyl group; Z is a single bond, —COO—, or —OCO—; $Q^1$ and $Q^2$ are H, F, CN, or CF$_3$, and at least one of Q1 and $Q^2$ is not H.

In another embodiment of the present invention, $R^1$ and $R^2$ are independently a straight chain or branched chain alkyl group having 5 to 8 carbon atoms, A and B are independently a phenylene group which can be substituted by halogen, a cyano group, a lower alkoxy group, or a fluorine-containing alkyl group, and Z is a single bond in Formula I or II.

In another embodiment of the present invention, the chiral compound is selected from the group consisting of a compound represented by the following Formulae and enantiomers thereof.

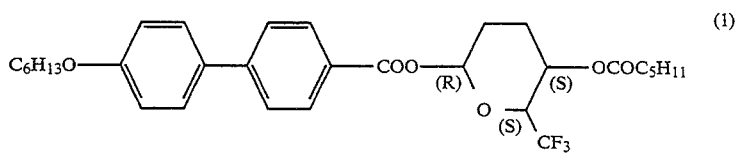

(1)

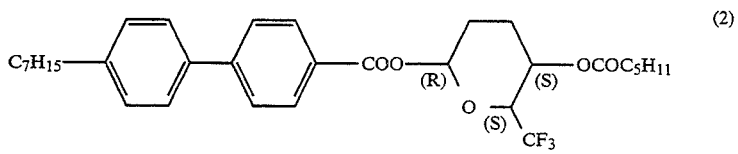

(2)

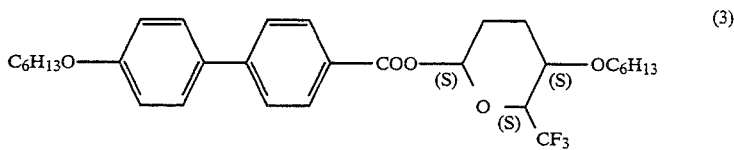

(3)

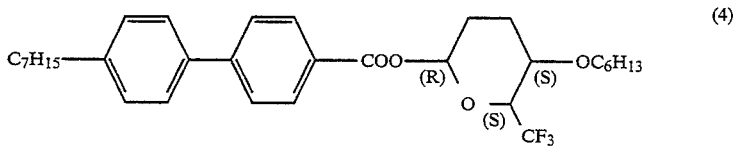

(4)

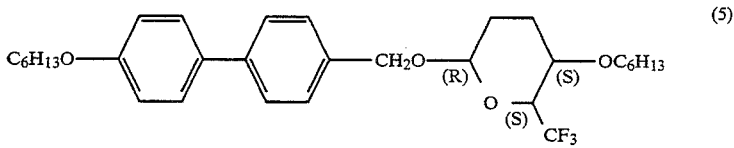

(5)

In another embodiment of the present invention, the chiral compound is selected from the group consisting of a compound represented by the following Formulae and enantiomers.

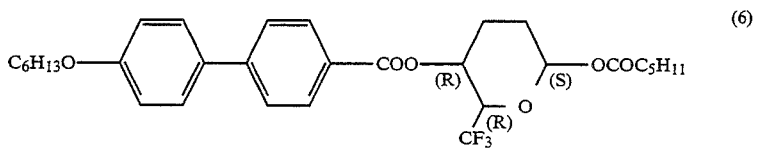

(6)

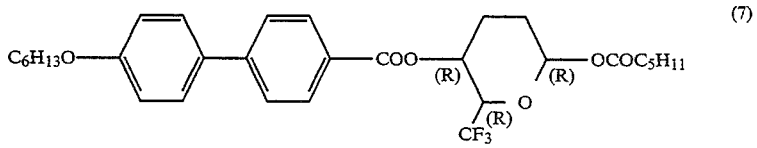

(7)

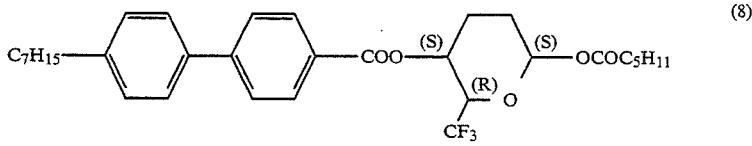

(8)

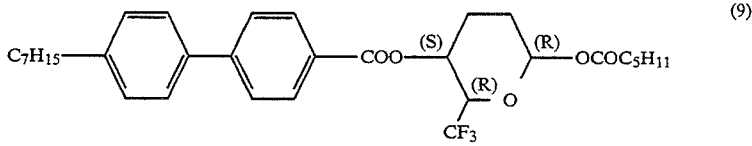

(9)

-continued

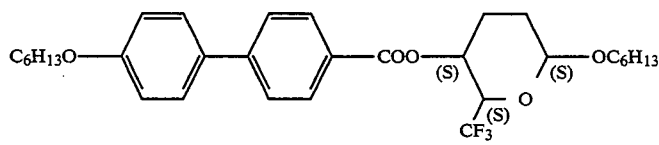
(10)

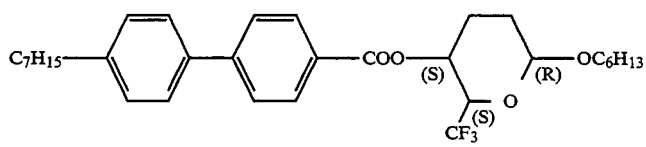
(11)

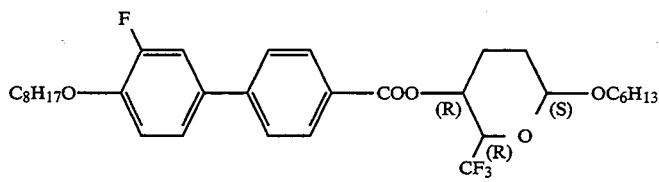
(12)

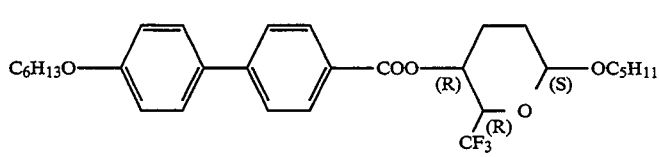
(13)

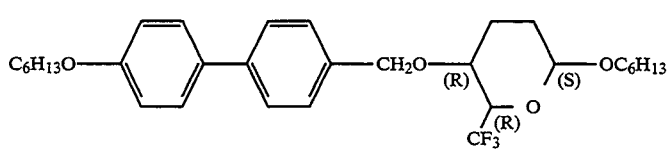
(14)

In another embodiment of the present invention, the above-mentioned ferroelectric liquid crystal mixture contains the compound represented by Formula I in an amount of 0.01 to 5 wt % based on the total amount of the ferroelectric liquid crystal mixture.

In another embodiment of the present invention, the above-mentioned ferroelectric liquid crystal mixture contains the compound represented by Formula II in an amount of 0.01 to 5 wt % based on the total amount of the ferroelectric liquid crystal mixture.

In another embodiment of the present invention, the compound represented by Formula I and the compound represented by Formula II are achiral compounds, and the achiral compounds are contained in the above-mentioned ferroelectric liquid crystal mixture in an amount of 5 to 20 wt % based on the total amount of the ferroelectric liquid crystal mixture.

According to another aspect of the present invention, a liquid crystal device comprises a pair of facing substrates, liquid crystal sandwiched between the pair of substrates, means for aligning the liquid crystal, and means for applying a voltage to the liquid crystal, wherein the liquid crystal is made of a ferroelectric liquid crystal mixture having negative dielectric anisotropy and exhibiting a chiral smectic C phase containing a compound selected from the group consisting of the compound represented by Formula I and the compound represented by Formula II.

In one embodiment of the present invention, the compound represented by Formula I and the compound represented by Formula II are chiral compounds.

Thus, the invention described herein makes possible the advantage of providing a ferroelectric liquid crystal mixture having a low local minimum value $V_{min}$ and a liquid crystal device using the same.

This and other advantages of the present invention will become apparent to those skilled in the art upon reading and understanding the following detailed description with reference to the accompanying figures.

BRIEF DESCRIPTION OF THE DRAWINGS

FIG. 3 is a diagram illustrating a principle of a method for driving using the driving waveforms of FIG. 2.

DESCRIPTION OF THE PREFERRED EMBODIMENTS

Synthesis Example

Figure 1A:
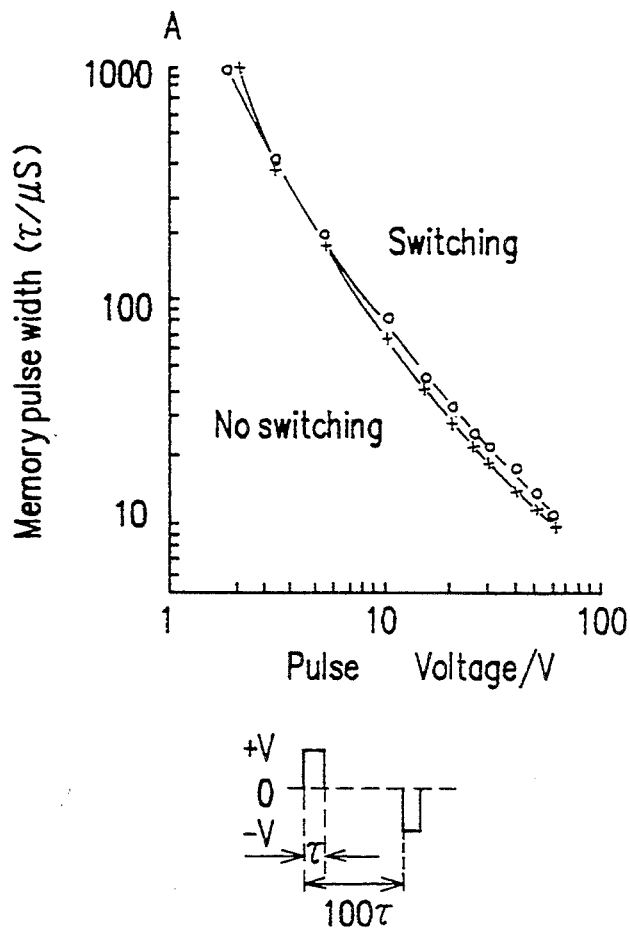
FIGS. 1A and 1B are graphs showing $\tau$-V characteristics of ferroelectric liquid crystal devices.
Figure 1B:
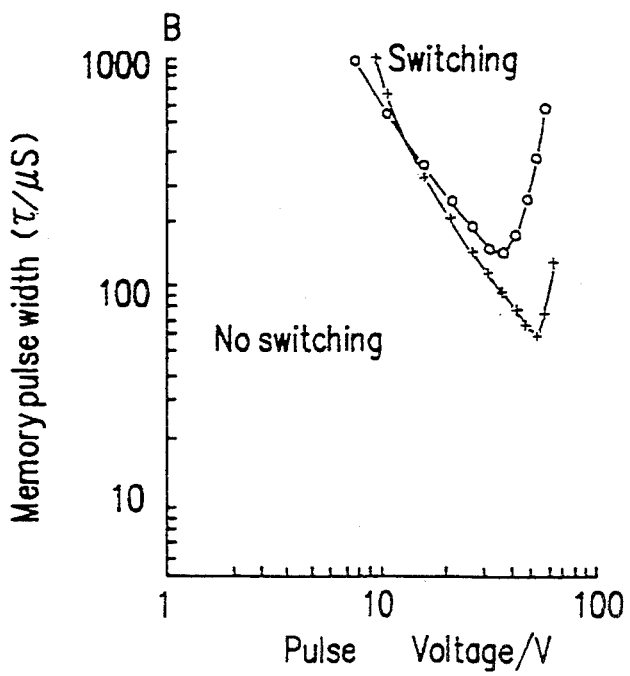

A method for synthesizing a compound contained in a ferroelectric liquid crystal mixture of the present invention will be described in the following order:

1. A method for synthesizing optically active substances (chiral compounds) represented by the following general Formulae IV to VII which are materials for compounds represented by Formulae I and II.

2. A method for synthesizing a compound represented by Formula I.

3. A method for synthesizing a compound represented by Formula II.

4. A method for synthesizing a known compound represented by Formula III.

In particular, a method for synthesizing chiral compounds represented by Formulae I and II will be described. The chiral compounds represented by Formulae I and II are synthesized using, as materials, optically active substances (chiral compounds) represented by Formulae IV to VII. In the case where achiral compounds (racemic bodies) represented by Formulae I and II are synthesized, achiral compounds represented by Formulae IV to VII can be used as materials.

1. Synthesis of optically active substances represented by Formulae IV to VII:

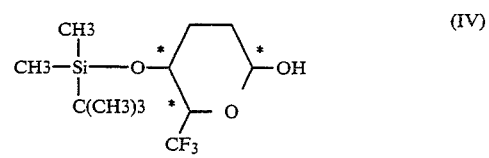
(IV)

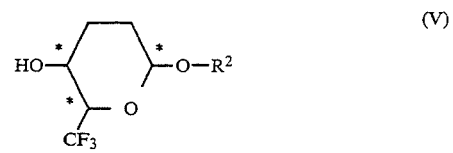
(V)

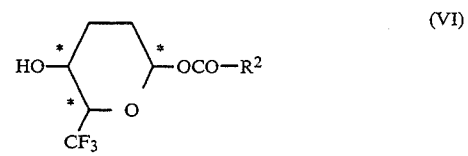
(VI)

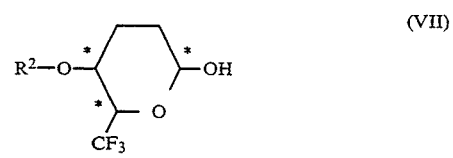
(VII)

where $R^2$ is a straight-chain or branched chain alkyl group having 1 to 15 carbon atoms, and * is asymmetric carbon.

Optically active substances represented by Formulae IV to VII can be synthesized as follows:

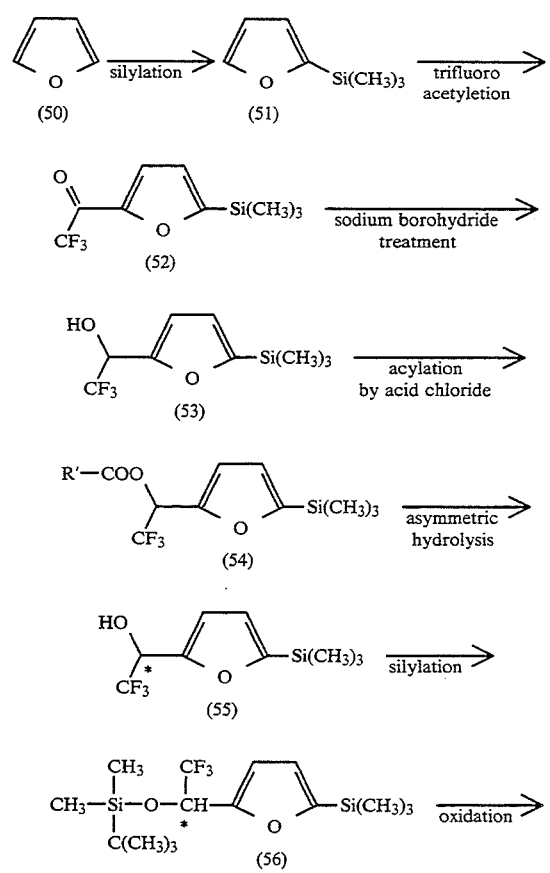

-continued

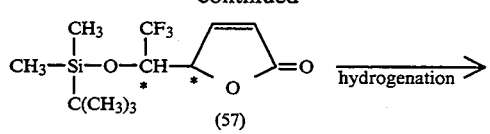

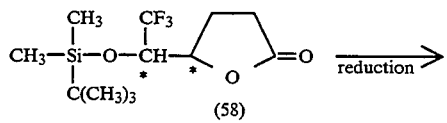

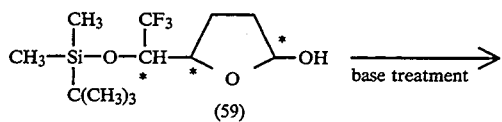

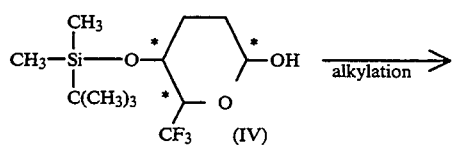

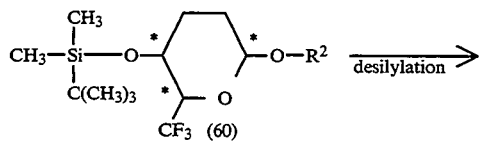

(IV) $\xrightarrow{\text{acylation}}$

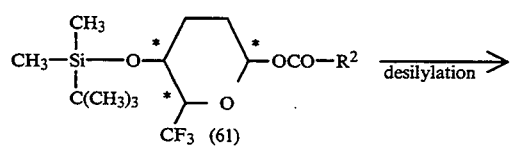

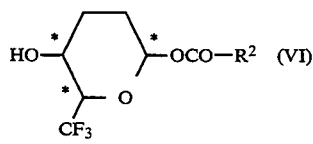

(V) $\xrightarrow{\text{alkylation}}$

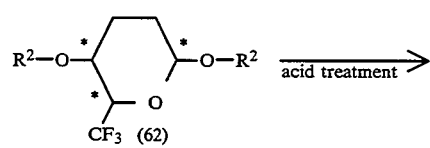

The above reaction can be carried out by a conventional method.

2. Synthesis of a chiral compound (compound with a $CF_3$ group facing outward) represented by Formula I:

$$R^1-X^1-A-Z-B-Y-\phantom{xxx}-X^2-R^2 \quad (I)$$

where $R^1$ and $R^2$ are the same or different straight-chain or branched chain alkyl groups having 1 to 15 carbon atoms; $X^1$ is a single bond, —O—, —COO—, or —OCO—; $X^2$ is —O— or —OCO—; Y is —COO— or —CH$_2$O; A and B are independently a group including a six membered ring which can be substituted by halogen, a cyano group, a lower alkoxy group, or a fluorine-containing alkyl group; and Z is a single bond, —COO—, or —OCO—.

(1) A compound represented by Formula I, where Z is a single bond, —COO—, or —OCO—; Y is —COO—; and $X^2$ is —O— can be synthesized by the following method, using the optically active substance represented by Formula VII as part of its material.

$$R^1-X^1-A-B-CO.Hal + \quad (VII)$$

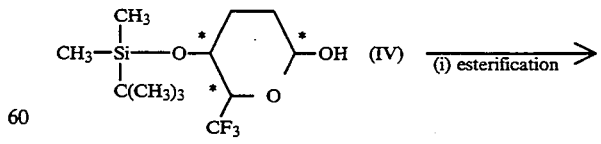

where $R^1$ and $R^2$ are the same or different straight-chain or branched chain alkyl groups having 1 to 15 carbon atoms; $X^1$ is a single bond, —O—, —COO—, or —OCO—; A and B are independently a group including a six membered ring which can be substituted by halogen, a cyano group, a lower alkoxy group, or a fluorine-containing alkyl group; and Hal is halogen.

The reaction in the above method can be carried out in a solvent such as toluene, benzene, and methylene chloride in the presence of an organic base such as pyridine and triethylamine at −20° C. to 80° C.

(2) A compound represented by Formula I, where Z is a single bond, Y is —COO—, and $X^2$ is —OCO—, can be synthesized by the following method, using the optically active substance represented by Formula IV as part of its material.

$$R^1-X^1-A-B-CO.Hal +$$

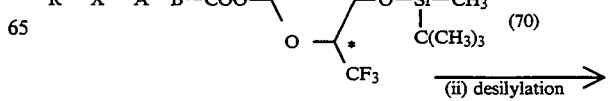

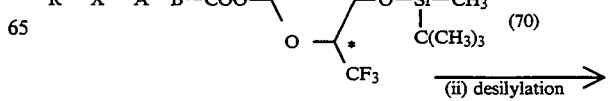

-continued

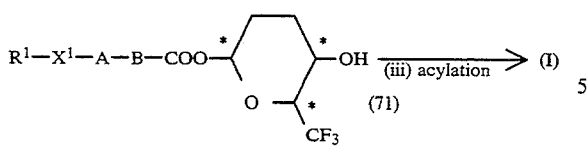

where $R^1$ and $R^2$ are the same or different straight-chain or branched chain alkyl groups having 1 to 15 carbon atoms; $X^1$ is a single bond, —O—, —COO—, or —OCO—; $X^2$ is —O— or —OCO—; A and B are independently a group including a six membered ring which can be substituted by halogen, a cyano group, a lower alkoxy group, or a fluorine-containing alkyl group; * is asymmetric carbon; and Hal is halogen.

The esterification (i) in the above method can be effected in a solvent such as toluene, benzene, and methylene chloride in the presence of an organic base such as pyridine and triethylamine in a temperature range of $-20°$ C. to $80°$ C.

The desilylation (ii) in the above method can be effected in a solvent of tetrahydrofran in a temperature range of $0°$ C. to $50°$ C., using tetra-n-butylammonium fluoride as a catalyst.

The acylation (iii) in the above method can be effected in a solvent such as toluene, benzene, and methylene chloride in the presence of an organic base such as pyridine and triethylamine in a temperature range of $-20°$ C. to $80°$ C.

(3) A compound represented by Formula I, where Z is a single bond, Y is —CH$_2$O—, and $X^2$ is —O—, can be synthesized by the following method, using the optically active substance represented by Formula VII as part of its material.

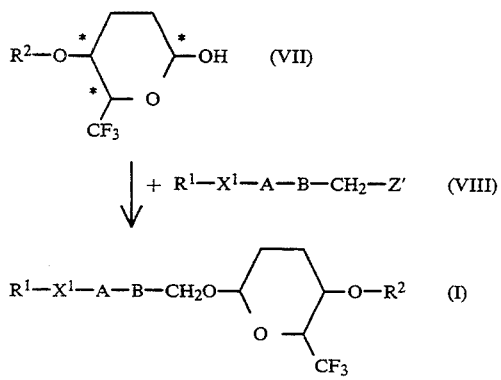

where $R^1$ and $R^2$ are the same or different straight-chain or branched chain alkyl groups having 1 to 15 carbon atoms; $X^1$ is a single bond, —O—, —COO—, or —OCO—; $X^2$ is —O— or —OCO—; A and B are independently a group including a six membered ring which can be substituted by halogen, a cyano group, a lower alkoxy group, or a fluorine-containing alkyl group; and Z' is chlorine, bromine, iodine, or a tosyl group.

The above-mentioned reaction is carried out by allowing a base such as an alkali metal hydride, sodium hydroxide, and potassium hydroxide to react with the compounds represented by Formula VII and adding the compound represented by Formula VIII to the reaction product.

3. Synthesis of a chiral compound (compound with a CF$_3$ group facing inward) represented by Formula II:

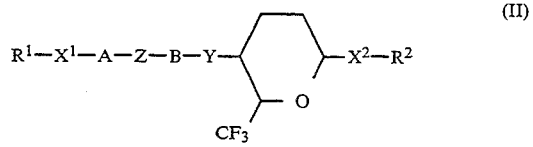

where $R^1$ and $R^2$ are the same or different straight-chain or branched chain alkyl groups having 1 to 15 carbon atoms; $X^1$ is a single bond, —O—, —COO—, or —OCO—; $X^2$ is —O— or —OCO—; Y is —COO— or —CH$_2$O—; A and B are independently a group including a six membered ring which can be substituted by halogen, a cyano group, a lower alkoxy group, or a fluorine-containing alkyl group; and Z is a single bond, —COO—, or —OCO—.

(1) A compound represented by Formula II, where Z is a single bond and Y is —COO—, can be synthesized by the following method, using the optically active substances represented by Formula V or VI as part of its material.

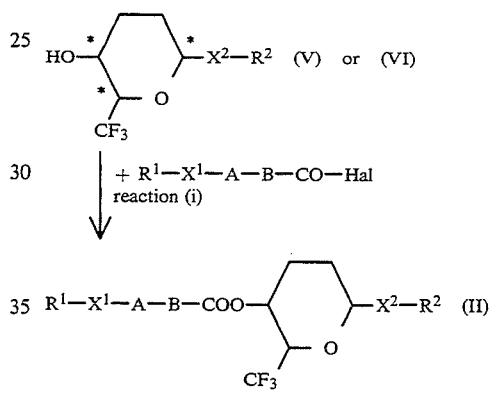

where $R^1$ and $R^2$ are the same or different straight-chain or branched chain alkyl groups having 1 to 15 carbon atoms; $X^1$ is a single bond, —O—, —COO—, or —OCO—; $X^2$ is —O— or —OCO—; A and B are independently a group including a six membered ring which can be substituted by halogen, a cyano group, a lower alkoxy group, or a fluorine-containing alkyl group; and Hal is halogen.

The reaction (i) in the above method can be carried out in a solvent such as toluene, benzene, and methylene chloride in the presence of an organic base such as pyridine and triethylamine in a temperature range of $-20°$ C. to $80°$ C.

(2) A compound represented by Formula II, where Z is a single bond and Y is —CH$_2$O—, can be synthesized by the following method, using the optically active substance represented by Formula V or VI as part of its material.

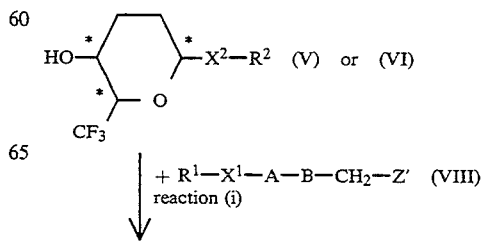

-continued

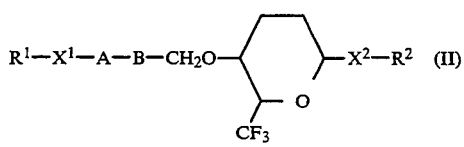

where $R^1$ and $R^2$ are the same or different straight-chain or branched chain alkyl groups having 1 to 15 carbon atoms; $X^1$ is a single bond, —O—, —COO—, or —OCO—; $X^2$ is —O— or —OCO—; A and B are independently a group including a six membered ring which can be substituted by halogen, a cyano group, a lower alkoxy group, or a fluorine-containing alkyl group; and $Z'$ is chlorine, bromine, iodine, or a tosyl group.

The reaction (i) in the above method can be carried out by allowing the compound represented by Formula V or VI to react with a base such as alkali metal hydride, sodium hydroxide and potassium hydroxide and then adding the compound represented by Formula VIII to the resulting reaction product.

(3) A compound represented by Formula II, where Z is —COO— and Y is —COO— can be synthesized by the following method, using the optically active substance represented by Formula V or VI as part of its material.

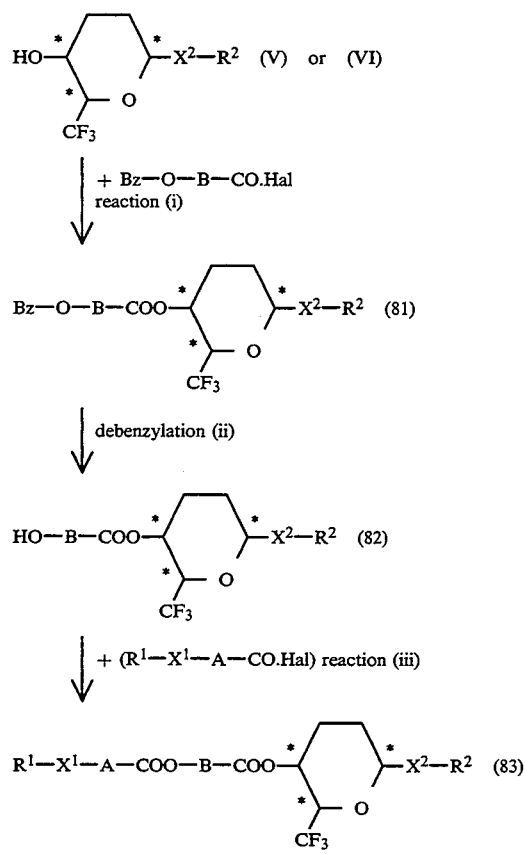

where $R^1$ and $R^2$ are the same or different straight-chain or branched chain alkyl groups having 1 to 15 carbon atoms; $X^1$ is a single bond, —O—, —COO—, or —OCO—; $X^2$ is —O— or —OCO—; A and B are independently a group including a six membered ring which can be substituted by halogen, a cyano group, a lower alkoxy group, or a fluorine-containing alkyl group; Hal is halogen; and Bz is a benzyl group.

The reaction (i) in the above method can be carried out in a solvent such as toluene, benzene, and methylene chloride in the presence of an organic base such as pyridine and triethylamine in a temperature range of $-20°$ C. to 80° C.

The debenzylation (ii) in the above method can be effected by hydrogenolysis at atmospheric pressure, using acetic acid or an alcoholic solvent such as methanol, ethanol, and propanol in the presence of, for example, a palladium carbon (Pd/C) catalyst.

The reaction (iii) in the above method can be carried out in a solvent of toluene, benzene, and methylene chloride in the presence of an organic base such as pyridine and triethylamine in a temperature range of $-20°$ C. to 80° C.

(4) A compound represented by Formula II, where Z is —COO— and Y is —CH$_2$O—, can be synthesized by the following method, using the optically reactive substance represented by Formulae V or VI as part of its material.

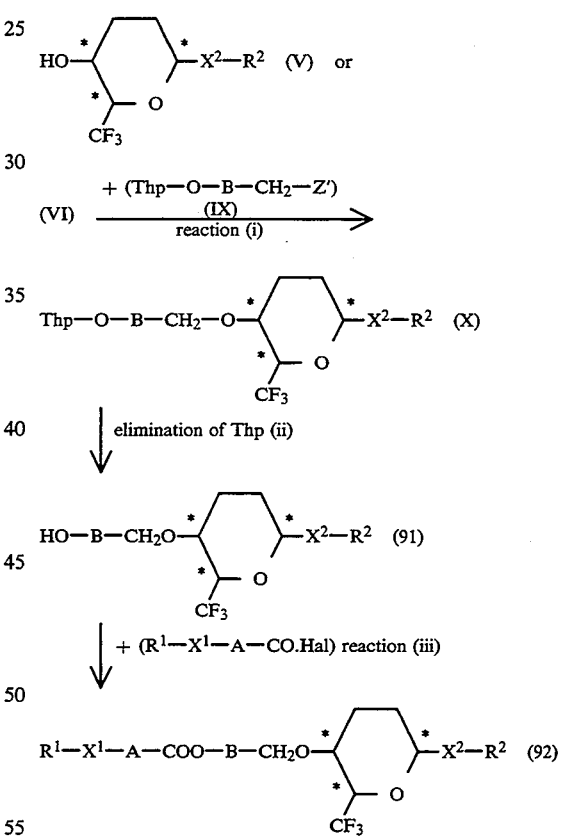

where $R^1$ and $R^2$ are the same or different straight-chain or branched chain alkyl groups having 1 to 15 carbon atoms; $X^1$ is a single bond, —O—, —COO—, or —OCO—; $X^2$ is —O— or —OCO—; A and B are independently a group including a six membered ring which can be substituted by halogen, a cyano group, a lower alkoxy group, or a fluorine-containing alkyl group; Hal is halogen; $Z'$ is chlorine, bromine, iodine, or a tosyl group; and Thp is a tetrahydropyranyl group.

The reaction (i) in the above method can be carried out by allowing the compound represented by Formula V or VI to react with a base such as an alkali metal hydride, sodium hydroxide, and potassium hydroxide and then adding the compound represented by Formula IX to the resulting reaction product.

The elimination (ii) of a tetrahydropyranyl group in the above method can be effected, using a solvent such as ether, tetrahydrofuran, and chloroform in the presence of an acid catalyst such as hydrochloric acid, sulfuric acid, and p-toluenesulfonic acid.

The reaction (iii) in the above method can be effected in a solvent such as toluene, benzene, and methylene chloride in the presence of an organic base such as pyridine and triethylamine in a temperature range of −20° C. to 80° C.

4. A known compound represented by Formula III can be synthesized by the conventional synthesis method. Examples of the conventional synthesis method are described in G. W. Gray, M. Hied and K. J. Toyne, Mol. Cryst. Liq. Cryst., 204, 43 (1991); Japanese Laid-Open Patent Publication Nos. 2-289529, 2-279649, 2-4725, 2-4724; and Japanese National Publication Nos. 2-504520, 2-502914, 2-503568, 2-503443, 2-503441, 2-503436, 2-503431, and 2-503430.

Hereinafter, the synthesis method will be described by way of illustrative synthesis examples.

SYNTHESIS EXAMPLE 1

As examples of compounds represented by Formulae IV to VII, (2R, 5S, 6S)-tetrahydro-6-trifluoromethyl-2-hexyloxy-5-hydroxypyrane and (2S, 5S, 6S)-tetrahydro-6-trifluoromethyl-2-hexyloxy-5-hydroxypyran were synthesized as follows:

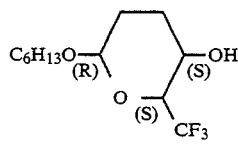 (101)

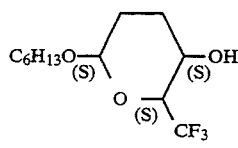 (102)

(a) First, 13.6 g (200 mM) of furan was added to 150 ml of tetrahydrofuran in an atmosphere of nitrogen. Then, 133 ml (200 mM) of hexane solution containing 1.5 mol/l of n-butyllithium was dropped into the mixture at −20° C. and allowed to react for one hour. To the reaction mixture, 21.7 g (200 mM) of trimethylsilyl chloride was dropped and stirred at −20° C. for one hour. To the resulting reaction mixture, 133 ml (200 mM) of hexane solution containing 1.5 mol/l of n-butyllithium was added and allowed to react at −20° C. for one hour. Then, 28.4 g (200 mM) of trifluoroethyl acetate was dropped into the reaction mixture thus obtained and allowed to react at −78° C. for one hour and at room temperature for another one hour. To the reaction solution, 3 N hydrochloric acid was added to stop the reaction, and the reaction solution was extracted with ethyl acetate. Then, the extract was washed successively with a saturated sodium hydrogen carbonate and brine and dried with magnesium sulfate anhydride. Ethyl acetate was removed from the extract under reduced pressure to obtain a crude product of a furan derivative.

(b) First, 2.3 g (60 mM) of sodium borohydride was added to 100 ml of dry ethanol. The crude product of the furan derivative obtained in the above reaction was dropped into the mixture at 0° C. over 30 minutes. The resulting mixture was allowed to react at room temperature for 2 hours, and ethanol was distilled under reduced pressure. To the reaction solution, 3 N hydrochloric acid was added to stop the reaction and extracted with ethyl acetate. Then, the extract was washed successively with a saturated sodium hydrogen carbonate and brine and dried with magnesium sulfate anhydride. Ethyl acetate was removed from the extract under reduced pressure, and then the extract was distilled under reduced pressure to obtain 40.5 g (170 mM) of alcohol compound.

(c) First, 23.8 g (100 mM) of alcohol compound obtained in the above reaction (b) and 8.9 ml (110 mM) of pyridine were added to 200 ml of methylene chloride. Then, 8.6 g (110 mM) of acetyl chloride was dropped into the mixture at 0° C. and allowed to react at room temperature for 12 hours. To the reaction solution, 3 N hydrochloric acid was added to stop the reaction and extracted with methylene chloride. The extract was washed successively with a saturated sodium hydrogen carbonate and distilled water and dried with magnesium sulfate anhydride. Methylene chloride was removed from the extract under reduced pressure, and then the extract was distilled under reduced pressure to obtain 27.5 g (98 mM) of ester compound.

(d) First, 28.0 g (100 mM) of ester compound obtained in the above reaction (c) was added to 1000 ml of distilled water and stirred in a mini-jar fermenter at 40° C. Then, 20 g of lipase PS (manufactured by Amano Pharmaceutical Co., Ltd.) was added to the mixture and allowed to react for 20 hours. To the reaction solution, 3 N hydrochloric acid was added and cooled to 0° C. to stop the reaction. The mixture was filtrated with sellite. The filtrate was extracted with ethyl acetate and washed with brine. The resulting filtrate was dried with magnesium sulfate anhydride, and ethyl acetate was removed under reduced pressure. Then, the resulting filtrate was separated to be purified by silica gel column chromatography to obtain 11.7 g (49 mM) of optically active alcohol compound and 13.2 g (47 mM) of optically active ester compound. The optical purity of the alcohol compound thus obtained was 97.5% e.e.

(e) First, 11.7 g (49 mM) of optically active alcohol compound obtained in the above reaction (d) was dissolved in 100 ml of methylene chloride. Then, 4.0 g (59 mM) of imidazole and 8.9 g (59 mM) of t-butyldimethylsilyl chloride were added to the solution at 0° C. and stirred for 15 minutes, followed by reacting at room temperature for 16 hours. To the reaction solution, distilled water was added to stop the reaction and extracted with methylene chloride. Then, the extract was washed with distilled water and dried with magnesium sulfate anhydride, and methylene chloride was removed under reduced pressure. Then, the resulting extract was separated to be purified by silica gel column chromatography to obtain 16.6 g (47 mM) of silylether compound.

(f) First, 14.1 g (40 mM) of silylether compound and 23.2 g (60 mM) of monoperoxymagnesium phthalate were added to 120 ml of acetic acid in an atmosphere of nitrogen and allowed to react at 80° C. for 12 hours. Then, acetic acid was removed under reduced pressure. To the resulting reaction mixture, saturated sodium hydrogen carbonate was added and extracted with ethyl acetate. Then, the extract was washed with brine and dried with magnesium sulfate anhydride. Ethyl acetate was removed under reduced pressure. The resulting extract was separated to be purified by silica gel column chromatography to obtain 4.7 g (16 mM) of (4S, 1'S) butenoride compound and 3.0 g (10 mM) of (4R, 1'S) butenoride compound. In this case, 4.2 g (12 mM) of unreacted material was also collected.

(g) First, 13.7 g (46 mM) of (4S, 1'S) and (4R, 1'S) butenoride compounds obtained in the above reaction (f) were dissolved in 40 ml of ethanol without being separated. Then, 1.4 g of 10% Pd/C (containing 10% by weight of Pd) was added to the solution and allowed to react in an atmosphere of hydrogen at room temperature for 15 hours. The reaction solution was filtrated and a solvent was removed under reduced pressure. Then, the filtrate was separated to be purified by silica gel column chromatography to obtain 3.2 g (29 mM) of (4S, 1'S) butanoride and 3.6 g (12 mM) of (4R, 1'S) butanoride compound.

(h) First, 7.5 g (25 mM) of (4S, 1'S) butanoride compound obtained in the above reaction (g) was added to 40 ml of diethyl ether in an atmosphere of nitrogen. Then, 32 ml (30 mM) of n-hexane solution containing 0.93 mol/l of diisobutylaluminium hydride was dropped into the mixture and allowed to react at −78° C. for 3 hours. To the reaction solution, distilled water was added to stop the reaction. Then, the solution was neutralized with 1N hydrochloric acid and was extracted with diethyl ether. The extract was washed with brine and dried with magnesium sulfate anhydride. Diethylether was removed from the extract under reduced pressure and the extract was purified by silica gel column chromatography to obtain 7.3 g (24 mM) of lactol compound.

(i) First, 7.3 g (24 mM) of lactol compound obtained in the above reaction (h) was added to 50 ml of tetrahydrofuran in an atmosphere of nitrogen. Then, 10 ml of tetrahydrofuran solution containing 3.0 g (27 mM) of potassium-t-butoxide was dropped into the mixture at about −78° C. and allowed to react for about 3 hours. To the reaction solution, distilled water was added to stop the reaction. Then, the solution was neutralized with 1N hydrochloric acid and extracted with diethyl ether. The extract was washed with brine and dried with magnesium sulfate anhydride. Diethyl ether was removed from the extract under reduced pressure and separated to be purified by silica gel column chromatography to obtain 6.4 g (21 mM) of pyranose compound.

(j) First, 6.4 g (21 mM) of pyranose compound obtained in the above reaction (i) was dissolved in 40 ml of hexanol. Then, 0.1 g of p-toluenesulfonic acid was added to the mixture and allowed to react at room temperature for about 18 hours. The reaction solution was purified by silica gel column chromatography to obtain 8.0 g (21 mM) of acetal compound. Although the acetal compound thus obtained was a diastereoisomer mixture, the acetal compound was used for the subsequent reaction without being separated.

(k) First, 8.0 g (21 mM) of acetal compound obtained in the above reaction (j) was dissolved in 20 ml of tetrahydrofuran. Then, 10 ml of tetrahydrofuran solution containing 1.0 mol/l of tetra-n-butylammonium fluoride was added to the mixture and allowed to react at about 0° C. for about one hour and at room temperature for about another 40 hours. To the reaction solution, distilled water was added to stop the reaction and extracted with diethyl ether.

Next, the extract was washed with brine and dried with magnesium sulfate anhydride. Diethyl ether was removed from the extract under reduced pressure and separated to be purified by silica gel column chromatography, thereby obtaining 3.0 g (11 mM) of intended (2R, 5S, 6S)-tetrahydro-6-trifluoromethyl-2-hexyloxy-5-hydroxypyran and 2.3 g (8 mM) of intended (2S, 5S, 6S)-tetrahydro-6-trifluoromethyl-2-hexyloxy-5-hydroxypyran.

The absolute configurations of the 5- and 6-positions of the compound thus obtained were identified using a method described in T. Yamazaki et al., J. Chem. Soc., Chem. Commun., 55, (1992). The absolute configuration of the 2-position was postulated from a coupling constant of protons at the 2- and 3-positions of a pyranose ring. The physical properties of the compound thus obtained are shown below.

1. (2R, 5S, 6S) compound
Molecular formula: $C_{12}H_{21}F_3O_3$
$^1$H-NMR (Proton nuclear magnetic resonance method); $\delta$(ppm)
 0.88 (t, J=6.5 Hz, 3H)
 1.20–1.39 (m, 6H)
 1.50–1.71 (m, 4H)
 1.83–2.04 (m, 2H)
 2.13–2.22 (m, 1H)
 3.46 (dt, J=9.4, 6.9 Hz, 1H)
 3.66 (dq, J=8.9, 6.3 Hz, 1H)
 3.81–3.93 (m, 2H)
 4.52 (dd, J=2.0, 8.7 Hz, 1H)
$^{19}$F-NMR (Isotope fluorine nuclear magnetic resonance method, Standard: $CFCl_3$); $\delta$(ppm)
 −75.13 (d, J=6.3 Hz)
IR (Infrared absorption: cm$^{-1}$) 3450, 1275, 1170, 1145, 1090, 940
Mass spectroscopy m/e (M$^+$+H)
Calculated value 271.1521
Measured value 271.1512
$[\alpha]_D^{25}$ −36.0° (C (concentration)=1.05, solvent: methanol)

2. (2S, 5S, 6S) compound
Molecular formula: $C_{12}H_{21}F_3O_3$
$^1$H-NMR; $\delta$(ppm)
 0.90 (t, J=7.3 Hz, 3H)
 1.23–1.45 (m, 6H)
 1.52–1.67 (m, 2H)
 1.76–2.00 (m, 5H)
 3.42 (dr, J=9.7, 6.4 Hz, 1H)
 3.68 (dt, J=9.7, 6.8 Hz, 1H)
 3.79–3.98 (m, 2H)
 4.86 (m, 1H)
$^{19}$F-NMR (Standard: $CFCl_3$); $\delta$(ppm)
 −75.17 (d, J=6.2 Hz)
IR(cm$^{-1}$) 3400, 1270, 1175, 1130, 1045, 945
Mass spectroscopy m/e (M$^+$+H)
Calculated value 271.1521
Measured value 271.1493
$[\alpha]_D^{25}$=−86.5° (C (concentration)=1.08 solvent: methanol)

SYNTHESIS EXAMPLE 2

As an example of a chiral compound represented by Formula I, (2S, 5R, 6R)-tetrahydro-6-trifluoro methyl-5-hexanoyloxy-2-(4''-hexyloxybiphenyl-4'-carbonyloxy)pran was synthesized as follows:

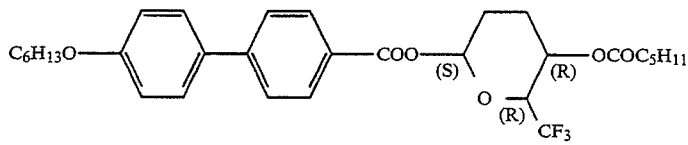

(a) First, 2 ml of pyridine anhydride was added to 5 ml of toluene solution containing 1.14 g (3.6 mM) of 4′-hexyloxy-4-biphenylcarboxylic acid chloride and 0.90 g (3.0 mM) of (5R, 6R)-tetrahydro-5-t-butyldimethylsiloxy-6-trifluoromethyl-2-hydroxypyran obtained by hydrolyzing the optically active ester compound obtained in Synthesis Example 1 under an alkali condition and allowed to react at room temperature for 20 hours. To the reaction solution, distilled water was added to stop the reaction, and the solution was extracted with ether. Then, the extract was washed with brine and dried with magnesium sulfate anhydride. Ether was removed from the extract under reduced pressure, and the resulting extract was purified by silica gel column chromatography to obtain 1.12 g (1.9 mM) of ester compound.

(b) First, 1.12 g of ester compound obtained in the above reaction (a) was dissolved in 10 ml of tetrahydrofuran. Then, 1.0 ml of tetrahydrofuran solution containing 1.0 mol/l of tetra-n-butylammonium fluoride was added to the mixture and allowed to react at 0° C. for one hour and at room temperature for another 6 hours. To the reaction solution, distilled water was added to stop the reaction. The reaction product was extracted with ether. Then, the extract was washed with brine and dried with magnesium sulfate anhydride. Ether was removed from the extract under reduced pressure. The extract was separated to be purified by silica gel chromatography to obtain 0.08 g (0.2 mM) of alcohol compound having asymmetric carbon of (2R, 5R, 6R) and 0.74 g (1.6 mM) of alcohol compound having asymmetric carbon of (2S, 5R, 6R).

(c) First, 0.08 g of alcohol compound having asymmetric carbon of (2R, 5R, 6R) obtained in the above reaction (b) was dissolved in 3 ml of toluene. Then, 0.5 ml of pyridine and 0.03 ml (0.2 mM) of hexanoyl chloride were successively added to the mixture and allowed to react at room temperature for about 20 hours. To the reaction solution, distilled water was added to stop the reaction. The reaction product was extracted with ether. Then, the extract was washed with brine and dried with magnesium sulfate anhydride. Ether was removed from the extract under reduced pressure. The resulting extract was separated to be purified by silica gel chromatography to obtain 0.09 g (0.2 mM) of intended compound, i.e., (2S, 5R, 6R)-tetrahydro-6-trifluoromethyl-5-hexanoyloxy-2-(4″-hexyloxybiphenyl-4′-carbonyloxy)-pyran.

The physical properties of the compound thus obtained will be shown below.
Molecular formula: $C_{31}H_{39}F_3O_6$
$^1$H-NMR; δ(ppm)
0.82–1.01 (m, 6H)
1.20–2.31 (m, 18H)
2.33 (t, J=7.5 Hz, 2H)
4.02 (t, J=6.6 Hz, 2H)
4.29 (dq, J=9.8, 5.9 Hz, 1H)
5.10–5.22 (m, 1H)
6.48 (m, 1H)
7.00 (d, J=8.8 Hz, 2H)
7.59 (d, J=8.8 Hz, 2H)
7.67 (d, J=8.4 Hz, 2H)
8.11 (d, J=8.5 Hz, 2H)
$^{19}$F-NMR (Standard: $CFCl_3$); δ(ppm)
−76.05 (d, J=5.9 Hz)
IR ($cm^{-1}$) 1740, 1730, 1605, 1500, 1265, 1170, 1070
Mass spectroscopy m/e (M$^+$)
Calculated value 564.2699
Measured value 564.2704
$[α]_D^{27}$ −51.6° (C (concentration)=0.92 solvent; chloroform)

Synthesis Example 3

As an example of a chiral compound represented by Formula I, (2S, 5R, 6R)-tetrahydro-6-trifluoromethyl-5-hexanoyloxy-2-(4″-heptylbiphenyl-4′-carbonyloxy)-pyran was synthesized.

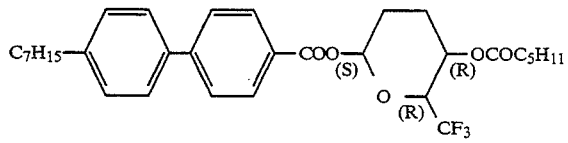

In the present Synthesis Example, 0.15 g (0.3 mM) of intended compound, i.e., (2S, 5R, 6R)-tetrahydro-6-trifluoromethyl-5-hexanoyloxy-2-(4″-heptylbiphenyl -4′-carbonyloxy)pyran was obtained by the same process as that of Synthesis Example 2 except that 0.74 g (2.4 mM) of 4′-heptyl-4-biphenylcarboxylic acid chloride was used.

The physical properties of the compound thus obtained will be shown.
Molecular formula: $C_{32}H_{41}F_3O_5$
$^1$H-NMR; δ(ppm)
0.82–0.97 (m, 6H)
1.18–1.45 (m, 11H)
1.53–1.76 (m, 5H)
1.94–2.29 (m, 4H)
2.33 (t, J=7.6 Hz, 2H)
2.67 (t, J=7.7 Hz, 2H)
4.29 (dq, J=9.8, 5.9 Hz, 1H)
5.10–5.23 (m, 1H)
6.49 (m, 1H)
7.30 (d, J=8.1 Hz, 2H)
7.56 (d, J=8.2 Hz, 2H)
7.70 (d, J=8.5 Hz, 2H)
8.13 (d, J=8.5 Hz, 2H)
$^{19}$F-NMR (Standard: $CFCl_3$); δ(ppm)
−76.07 (d, J=5.9 Hz)
IR ($cm^{-1}$) 1735, 1610, 1490, 1265, 1170, 1070
Mass spectroscopy m/e (M$^+$)
Calculated value 562.2906
Measured value 562.2934
$[α]_d^{25}$ −50.3° (C (concentration)=0.68 solvent: chloroform)

Synthesis Example 4

As an example of a chiral compound represented by Formula (I), (2S, 5S, 6S)-tetrahydro-6-trifluoromethyl-5-hexyloxy-2-(4″-hexyloxybiphenyl -4′-carbonyloxy)-pyran was synthesized as follows:

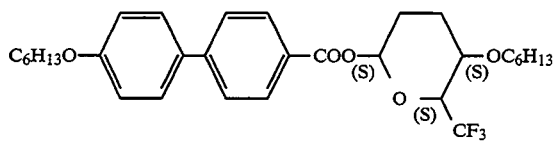

(a) First, 6.4 g (21 mM) of 5S, 6S)-tetrahydro-5-t-butyldimethylsiloxy-6-trifluoromethyl-2-hydroxypyran was dissolved in 40 ml of hexanol. Then, 0.1 g of p-toluenesulfonic acid was added to the mixture and allowed to react at room temperature for 18 hours. The reaction solution was purified by silica gel column chromatography to obtain 8.0 g (21 mM) of acetal compound.

(b) First, 8.0 g of acetal compound obtained in the reaction (a) of Synthesis Example 4 was dissolved in 20 ml of tetrahydrofuran. Then, 10 ml of tetrahydrofuran solution containing 1.0 mol/l of tetra-n-butylammonium fluoride was added to the mixture and allowed to react at 0° C. for one hour and at room temperature for another 40 hours. To the reaction solution, distilled water was added to stop the reaction. The reaction product was extracted with ether. Then, the extract was washed with saturated salt water solution and dried with magnesium sulfate anhydride. Ether was removed from the extract under reduced pressure. The resulting extract was separated to be purified by silica gel column chromatography to obtain 3.0 g (11 mM) of alcohol compound having asymmetric carbon of (2R, 5S, 6S) and 2.3 g (8.0 mM) of alcohol compound having asymmetric carbon of (2S, 5S, 6S).

(c) First, 5 ml of tetrahydrofuran solution containing 0.56 g (2.1 mM) of alcohol compound having asymmetric carbon of (2R, 5S, 6S) obtained in the reaction (b) of Synthesis Example 4 was dropped into 3 ml of tetrahydrofuran containing 0.10 g (2.5 mM) of 60% sodium hydride in an atmosphere of nitrogen at 0° C. and stirred for 30 minutes.

Next, 0.35 ml (2.5 mM) of 1-bromohexane and 2 ml of dimethylsulfoxide were added to the solution and allowed to react at room temperature for 18 hours. To the reaction solution, distilled water was added to stop the reaction. The reaction product was extracted with ether. Then, the extract was washed with saturated salt water solution and dried with magnesium sulfate anhydride. Ether was removed from the extract under reduced pressure. The resulting extract was purified by silica gel column chromatography to obtain 0.72 g (2.0 mM) of ether compound.

(d) First, 0.52 g (1.5 mM) of ether compound obtained in the reaction (c) of Synthesis Example 4 was dissolved in 10 ml of tetrahydrofuran. Then, 10 ml of distilled water and 2 ml of concentrated sulfuric acid were added to the mixture and refluxed for 50 hours. To the solution, 1N aqueous solution of potassium hydroxide was added to stop the reaction. The reaction product was extracted with ether. Then, the extract was washed with saturated salt water solution and dried with magnesium sulfate anhydride. Ether was removed from the extract under reduced pressure. The resulting extract was separated to be purified by silica gel column chromatography to obtain 0.37 g (1.4 mM) of hemiacetal.

(e) The intended compound, i. e. , (2S, 5S, 6S) -tetrahydro-6-trifluoromethyl-5-hexyloxy-2-(4″-hexyloxybiphenyl -4′-carbonyloxy)pyran was obtained in an amount of 0.34 g (0.6 mM) by the same process as that of the reaction (a) of Synthesis Example 2 except that 0.29 g (1.1 mM) of hemiacetal compound obtained in the reaction (d) of Synthesis Example 4 and 0.49 g (1.6 mM) of 4′-hexyloxy-4-biphenylcarboxylic acid chloride were used.

The physical properties of the compound thus obtained will be shown.

Molecular formula: $C_{31}H_{41}F_3O_5$
$^1$H-NMR; δ(ppm)
0.81–0.99 (m, 6H)
1.19–1.68 (m, 15H)
1.70–1.93 (m, 4H)
2.12–2.25 (m, 1H)
2.29–2.42 (m, 1H)
3.40–3.65 (m, 3H)
4.01 (t, J=6.6 Hz, 2H)
6.14 (dd, J=2.7, 6.6 Hz, mH)
6.98 (d, J=8.8 Hz, 2H)
7.56 (d, J=8.8 Hz, 2H)
7.62 (d, J=8.5 Hz, 2H)
8.10 (d, J=8.4 Hz, 2H)
$^{19}$F-NMR (Standard: $CFCl_3$); δ(ppm)
−74.98 (d, J=7.4 Hz)
IR ($cm^{-1}$) 1730, 1605, 1495, 1265, 1180,
Mass spectroscopy m/e ($M^+$)
Calculated value 550.2906
Measured value 550.2914
$[α]_D^{26} = +10.7°$ (C (concentration)=1.03, solvent: chloroform)

Synthesis Example 5

As a chiral compound represented by Formula II, (2R, 5R, 6R) -tetrahydro-6-trifluoromethyl-2-hexyloxy-5-(4″-hexyloxybiphenyl-4′-carbonyloxy)pyran was synthesized as follows:

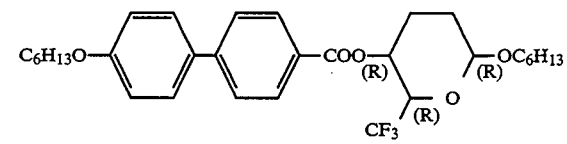

First, 1 ml of pyridine anhydride was added to 5 ml of toluene solution containing 0.32 g (1.0 mM) of 4′-hexyloxy-4-biphenylcarboxylic acid chloride and 0.28 g (0.8 mM) of (2R, 5R, 6R)-tetrahydro-6-trifluoromethyl-2-hexyloxy-5-hydroxypyran obtained by the same process as that of Synthesis Example 1 and allowed to react at room temperature for about 24 hours. To the reaction solution, distilled water was added to stop the reaction. The reaction solution was extracted with ether. Then, the extract was washed with saturated salt water solution and dried with magnesium sulfate anhydride. Ether was removed from the extract under reduced pressure. The resulting extract was purified by silica gel column chromatography to obtain 0.25 g (0.5 mM) of intended compound, i.e., (2R, 5R, 6R)-tetrahydro-6-trifluoromethyl-2-hexyloxy-5-(4″-hexyloxybiphenyl-4′-carbonyloxy)pyran.

The physical properties of the compound thus obtained will be shown.

Molecular formula: $C_{31}H_{41}F_3O_5$
$^1$H-NMR; δ(ppm)
0.87–1.02 (m, 6H)
1.26–2.24 (m, 20H)
3.48 (dr, J=9.7, 6.5 Hz, 1H)
3.75 (dr, J=9.7, 6.8 Hz, 1H)
4.00 (t, J=6.5 Hz, 2H)
4.30 (dq, J=9.8, 6.3 Hz, 1H)
4.94 (m, 1H)
5.25 (ddd, J=5.3, 9.7, 9.8 Hz, 1H)
6.98 (d, J=8.7 Hz, 2H)
7.55 (d, J=8.7 Hz, 2H)
7.62 (d, J=8.4 Hz,
8.06 (d, J=8.3 Hz, 2H)
$^{19}$F-NMR (Standard: CFCl$_3$); δ(ppm)
−75.98 (d, J=6.3 Hz)
IR(cm$^{-1}$) 1725, 1605, 1495, 1260, 1170,
Mass spectroscopy m/e (M$^+$)
Calculated value 550.2906
Measured value 550.2908
$[α]_D^{27} = -66.9°$ (C (concentration)=0.51 solvent: chloroform)

Synthesis Example 6

As an example of a chiral compound represented by Formula II, (2R, 5S, 6S)-tetrahydro-6-trifluoromethyl-2-hexyloxy-5-(4″-hexyloxybiphenyl-4′-carbonyloxy)pyran was synthesized.

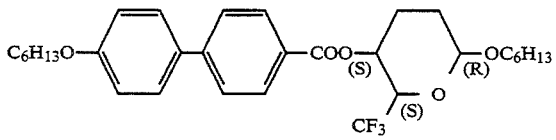

In the present Synthesis Example, 0.44 g (0.8 mM) of intended compound, i.e., (2R, 5S, 6S)-tetrahydro -6-trifluoromethyl-2-hexyloxy-5-(4″-hexyloxybiphenyl-4′-carbonyloxy)pyran was obtained by the same process as that of Synthesis Example 5 except that 0.49 g of 4′-hexyloxy-4-biphenylcarboxylic acid chloride and 0.35 g (1.3 mM) of (2R, 5S, 6S)-tetrahydro-6-trifluoromethyl-2-hexyloxy-5-hydroxypyran obtained in Synthesis Example 1 were used.

The physical properties of the compound thus obtained will be shown.

Molecular formula: $C_{31}H_{41}F_3O_5$
$^1$H-NMR; δ(ppm)
0.86–0.99 (m, 6H)
1.23–2.07 (m, 19H)
2.39–2.48 (m, 1H)
3.49 (dr, J=9.4, 6.8 Hz, 1H)
3.92 (dt, J=9.5, 6.7 Hz, 1H)
4.00 (t, J=6.6 Hz, 2H)
4.07 (dq, J=8.8, 6.3 Hz, 1H)
4.65 (dd, J=2.1, 8.2 Hz, 1H)
5.22 (ddd, J=5.0, 9.0, 9.5 Hz, 1H)
6.98 (d, J=6.8 Hz, 2H)
7.55 (d, J=8.7 Hz, 2H)
7.62 (d, J=8.5 Hz, 2H)
8.04 (d, J=8.4 Hz, 2H)
$^{19}$F-NMR (Standard: CFCl$_3$); δ(ppm)
−75.79 (d, J=6.3 Hz)
IR(cm$^{-1}$) 1720, 1610, 1500, 1260, 1190,
Mass spectroscopy m/e (M$^+$)
Calculated value 550.2906
Measured value 550.2899
$[α]_D^{25} = -13.0°$ (C (concentration) 1.10 solvent: chloroform)

Synthesis Example 7

As an example of a chiral compound represented by Formula II, (2R, 5S, 6S) -tetrahydro-6-trifluoromethyl-2-hexyloxy-5-(4″-heptylbiphenyl -4′-carbonyloxy)pyran was synthesized as follows:

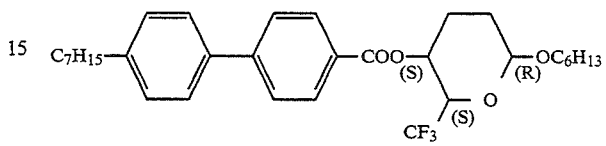

In the present Synthesis Example, 0.36 g (0.7 mM) of intended compound, i.e., (2R, 5S, 6S)-tetrahydro -6-trifluoromethyl-2-hexyloxy-5-(4″-heptylbiphenyl-4′-carbonyloxy)pyran was obtained by the same process as that of Synthesis Example 5 except that 0.38 g (1.2 mM) of 4′-heptyl-4-biphenylcarboxylic acid chloride and 0.27 g (1.0 mM) of (2R, 5S, 6S)-tetrahydro -6-trifluoromethyl-2-hexyloxy-5-hydroxypyran obtained in Synthesis Example 1 were used.

The physical properties of the compound thus obtained will be shown.

Molecular formula: $C_{32}H_{43}F_3O_4$
$^1$H-NMR; δ(ppm)
0.83–0.98 (m, 6H)
1.22–2.08 (m, 21H)
2.39–2.50 (m, 1H)
2.66 (t, J=7.7 Hz, 2H)
3.50 (dr, J=9.4, 6.9 Hz, 1H)
3.92 (dr, J=9.4, 6.7 Hz, 1H)
4.08 (dq, J=8.8, 6.3 Hz, 1H)
4.65 (dd, J=2.0, 8.1 Hz, 1H)
5.23 (ddd, J=5.0, 9.0, 9.3 Hz, 1H)
7.28 (d, J=8.1 Hz, 2H)
7.54 (d, J=8.1 Hz, 2H)
7.65 (d, J=8.4 Hz, 2H)
8.06 (d, J=8.4 Hz, 2H)
$^{19}$F-NMR (Standard: CFCl$_3$); δ(ppm)
−75.76 (d, J=6.3 Hz)
IR(cm$^{-1}$) 1710, 1610, 1495, 1260, 1180, 1050
Mass spectroscopy m/e (M$^+$)
Calculated value 548.3114
Measured value 548.3086
$[α]_D^{27} = -14.5°$ (C (concentration)=1.02 solvent: chloroform)

Other compounds represented by Formulae I and II used for the ferroelectric liquid crystal mixture of the present invention can be synthesized by the same processes as those of the above-mentioned Synthesis Examples.

Examples of the alkyl group having 1 to 15 carbon atoms represented by $R^1$ and $R^2$ in Formulae I and II include methyl, ethyl, n-propyl, n-butyl, isobutyl, n-pentyl, isopentyl, n-hexyl, isohexyl, n-heptyl, isoheptyl, n-octyl, isooctyl, n-nonyl, isononyl, n-decyl, isodecyl, n-undecyl, isoundecyl, n-dodecyl, isododecyl, n-tridecyl, isotridecyl, n-tetradecyl, isotetradecyl, n-pentadecyl, and isopentadecyl. Asymmetric carbon can be contained in a carbon chain of these alkyl groups. In addition, one or more hydrogen in these alkyl groups can be substituted by fluorine, chlorine, bromine, a cyano group, a nitro group, a trifluoromethyl group, a methoxy group, or the like. Examples of the group obtained by substituting one or more hydrogen in these alkyl groups include 1-trifluoromethylheptyl, 1-fluorooctyl, and 1-chloro-2-methyl-butyl.

Examples of the group including a six membered ring represented by A and B include heterocyclic groups including a six membered ring having one or two nitrogen atoms (e.g., pyridine-2,5-diyl, pyrimidine-2,5-diyl, pyridazine-3,6-diyl); aromatic hydrocarbon groups (e.g., phenylene, nephthalene-2,6-diyl); and saturated hydrocarbon group including a six membered ring which can have one or two oxygen atoms (e.g., cyclohexadinyl, tetrahydropyran-2,5-diyl, dioxane-2,5diyl). These groups including a six membered ring can be substituted by one or two groups selected from a halogen group (e.g., chloro, fluoro), a cyano group, a lower alkoxy group (e.g., methoxy, ethoxy), and a fluorine-containing alkyl group (e.g., monofluoromethyl, difluoromethyl, trifluoromethyl, monofluoroethyl). Preferred examples of the group including a six membered ring are as follows:

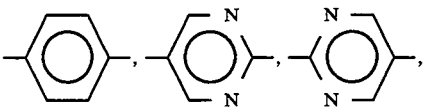

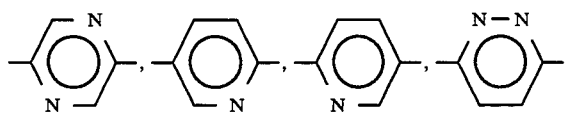

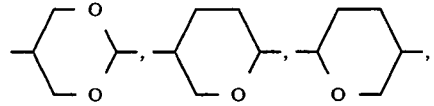

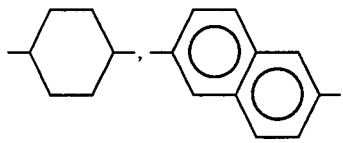

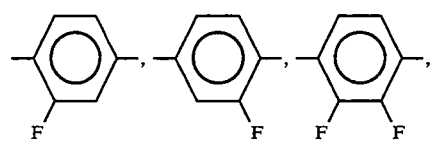

-continued

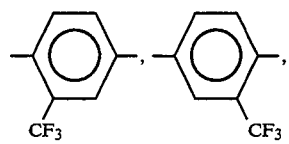

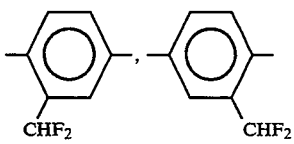

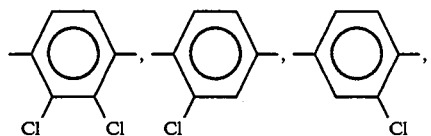

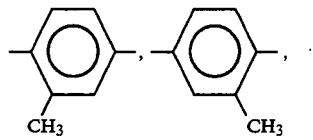

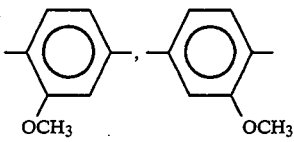

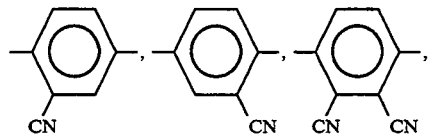

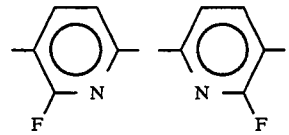

Examples of the chiral compound represented by Formula I include the following compounds and enantiomers thereof.

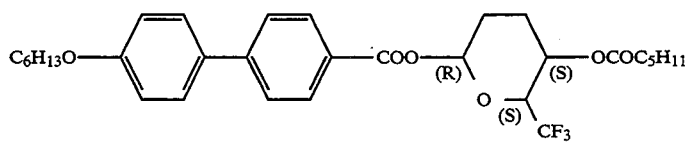

(1)

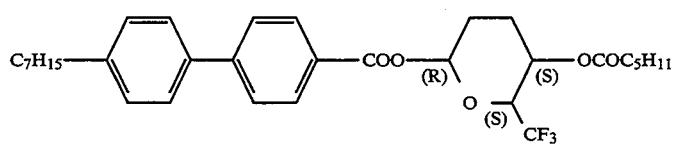

(2)

-continued
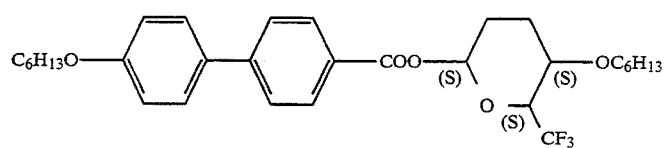 (3)
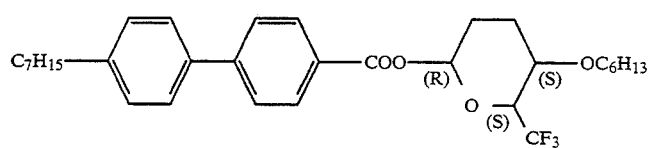 (4)
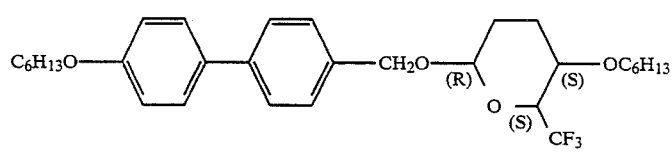 (5)
Examples of the chiral compound represented by Formula IT include the following compounds and enantiomers thereof.
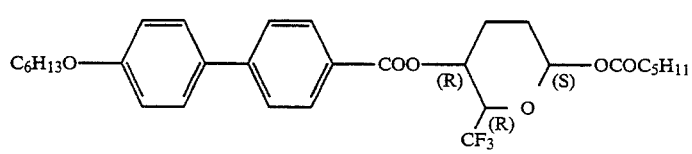 (6)
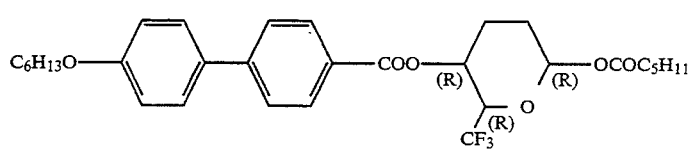 (7)
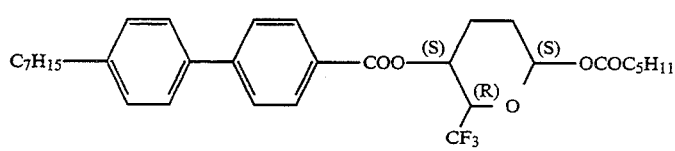 (8)
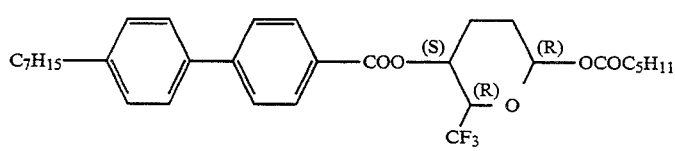 (9)
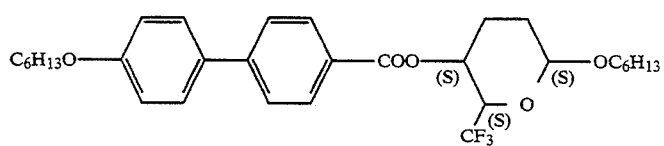 (10)
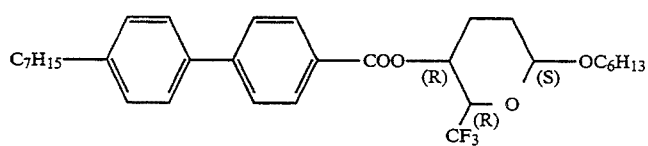 (11)

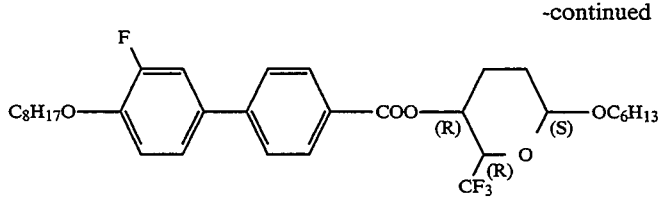
(12)

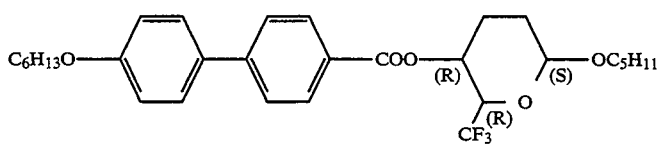
(13)

and

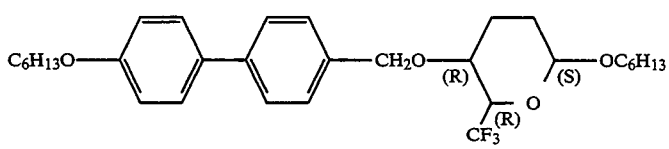
(14)

The ferroelectric liquid crystal mixture of the present invention can be prepared by adding the chiral compound represented by Formula I or II to a liquid crystal mixture having negative dielectric anisotropy and exhibiting a smectic C phase. The chiral compound represented by Formula I or II can be used alone or in combination of two or more kinds thereof. The chiral compound represented by Formula I or II can be used together with other known chiral compounds.

The ferroelectric liquid crystal mixture of the present invention can also be prepared by adding the achiral compound (racemic body) represented by Formula I or II to a ferroelectric liquid crystal mixture having negative dielectric anisotropy and exhibiting a chiral smectic C phase. In the case of using the achiral compound represented by Formula I or II, the chiral compound to be added to the liquid crystal mixture can be the chiral compound represented by Formula I or II, other known chiral compounds, or mixtures of these compounds.

The chiral compound represented by Formula I or II to be added to the liquid crystal mixture regulates the helical pitch of a liquid crystal phase, thereby improving orientation of liquid crystal molecules. The chiral compound is added to the liquid crystal mixture preferably in an amount of 0.01 to 5 wt %, more preferably 0.01 to 3 wt %. When the added amount of the compound is less than 0.01 wt %, the compound does not sufficiently work as a chiral agent. When the added amount of the compound is more than 5 wt %, the spontaneous polarization of the mixture becomes too large, so that $V_{min}$ becomes too high to drive. In the case of using the achiral compound represented by Formula I or II, the achiral compound is added to the ferroelectric liquid crystal mixture preferably in an amount of 5 to 20 wt %.

Examples of the liquid crystalline compound used for the ferroelectric liquid crystal mixture of the present invention include liquid crystalline compounds of an ester type, biphenyl type, terphenyl type, pyrimidine type, pyridine type, or the like; and liquid crystalline compounds obtained by substituting a hydrogen atom in a lateral direction of these liquid crystalline compounds by a halogen atom, a CN group, or the like. These liquid crystalline compounds are represented by Formula III.

Specific compounds included those represented by Formula III are as follows:

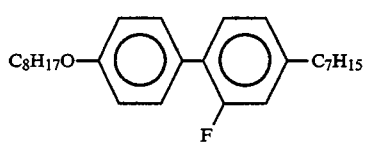
(15)

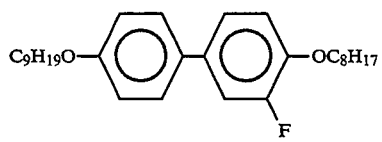
(16)

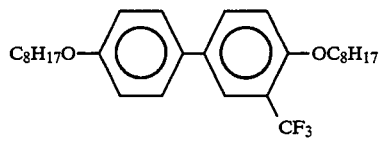
(17)

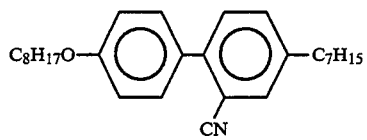
(18)

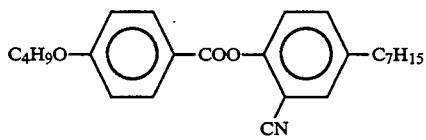
(19)

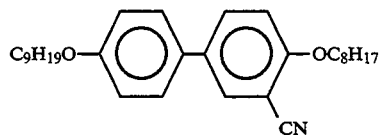
(20)

-continued

-continued

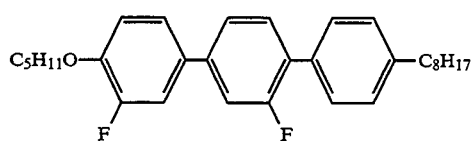 (41)

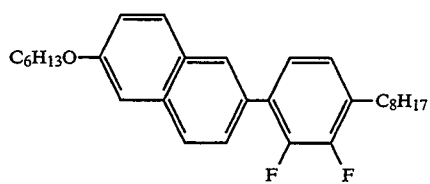 (42)

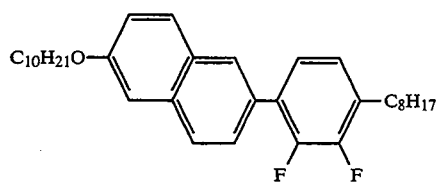 (43)

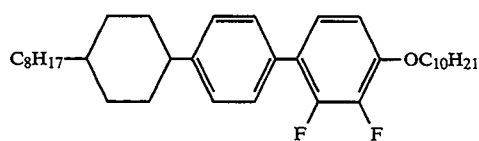 (44)

-continued

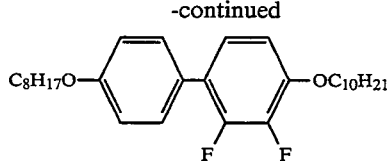 (45)

The above-mentioned liquid crystalline compounds can be appropriately mixed. Among the liquid crystal mixtures having negative dielectric anisotropy and exhibiting a smectic C phase, liquid crystal mixtures exhibiting a phase sequence of Isotropic-Smectic A-Smectic C (IAC) or Isotropic-Nematic-Smectic A-Smectic C (INAC) are particularly preferred because of their satisfactory orientation property and bistability.

Examples 1 to 5

Ferroelectric liquid crystal mixtures FLC1 to FLC5 of the present invention were prepared. In each of these examples, a ferroelectric liquid crystal mixture was prepared by adding the chiral compound represented by Formula I or II to a liquid crystal mixture made of the liquid crystalline compound represented by Formula III.

First, chiral compounds represented by Formula I or II shown in Table 1 were obtained in accordance with Synthesis Examples. Then, each of the chiral compounds thus obtained was added in an amount of 2 wt % to an achiral liquid crystal mixture shown in Table 2 to obtain ferroelectric liquid crystal mixtures. The transition temperature, response time, spontaneous polarization, helical pitch in a chiral nematic phase, and tilt angle are also shown in Table 1.

TABLE 1

| No. | Structural formula | Transition temperature (°C.) SC* Sa N* I | Reponse time (μsec) | Ps (nC/cm²) | N* (μm) | Tilt angle (deg) |
|---|---|---|---|---|---|---|
| KLC-339SA | C₆H₁₃O–⟨biphenyl⟩–COO–CH(S)–CH₂–CH(S)–O–CH(S)(CF₃)–OC₆H₁₃ | 45 62 67 | 81 | +3.6 | (+14) | 17 |
| KLC-340SA | C₆H₁₃O–⟨biphenyl⟩–COO–CH(S)–CH₂–CH(R)–O–CH(S)(CF₃)–OC₆H₁₃ | 49 63 69 | 91 | +4.3 | (−8) | 20 |
| KLC-340RA | C₆H₁₃O–⟨biphenyl⟩–COO–CH(R)–CH₂–CH(S)–O–CH(R)(CF₃)–OC₆H₁₃ | 49 63 69 | 75 | −3.7 | +8 | 20 |
| KLC-342SA | C₇H₁₅–⟨biphenyl⟩–COO–CH(S)–CH₂–CH(R)–O–CH(S)(CF₃)–OC₆H₁₃ | 49 62 68 | 74 | +4.6 | −7 | 20 |
| KLC-417RA | C₈H₁₇O–⟨biphenyl-F⟩–COO–CH(R)–CH₂–CH(S)–O–CH(R)(CF₃)–OC₆H₁₃ | 50 62 68 | 88 | −4.7 | +10 | 20 |
| KLC-433RB | C₆H₁₃O–⟨biphenyl⟩–COO–CH(R)–CH₂–CH(S)–O–CH(R)(CF₃)–OC₅H₁₁ | 49 63 69 | 84 | −4.4 | +9 | 19 |

TABLE 1-continued

| No. | Structural formula | Transition temperature (°C.) SC* Sa N* I | Reponse time (μsec) | Ps (nC/cm²) | N* (μm) | Tilt angle (deg) |
|---|---|---|---|---|---|---|
| KLC-375SA | C₆H₁₃O–⟨⟩–⟨⟩–COO(R)–⟨⟩–(S)OCOC₅H₁₁ / (S)CF₃ | 43 62 66 | 60 | −5.2 | (−22) | 17 |
| KLC-375RA | C₆H₁₃O–⟨⟩–⟨⟩–COO(S)–⟨⟩–(R)OCOC₅H₁₁ / (R)CF₃ | 44 63 67 | 54 | +5.4 | +22 | 17 |
| KLC-375SB | C₆H₁₃O–⟨⟩–⟨⟩–COO(R)–⟨⟩–(S)OCOC₅H₁₁ / (R)CF₃ | 43 62 67 | 67 | −5.0 | −26 | 16 |
| KLC-376SA | C₇H₁₅–⟨⟩–⟨⟩–COO(R)–⟨⟩–(S)OCOC₅H₁₁ / (S)CF₃ | 42 61 66 | 52 | −5.4 | −27 | 16 |
| KLC-372SA | C₆H₁₃O–⟨⟩–⟨⟩–COO(S)–⟨⟩–(S)OC₆H₁₃ / (S)CF₃ | 52 62 69 | 82 | +5.9 | +18 | 22 |
| KLC-372RA | C₆H₁₃O–⟨⟩–⟨⟩–COO(R)–⟨⟩–(R)OC₆H₁₃ / (R)CF₃ | 52 62 69 | 75 | −6.1 | −14 | 22 |

TABLE 1-continued
| No. | Structural formula | Transition temperature (°C.) SC* Sa N* I | Reponse time (μsec) | Ps (nC/cm²) | N* (μm) | Tilt angle (deg) |
|---|---|---|---|---|---|---|
| KLC-373SA | 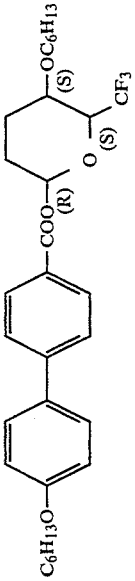 | 44 62 66 | 50 | −6.9 | −16 | 16 |
| KLC-437SA | 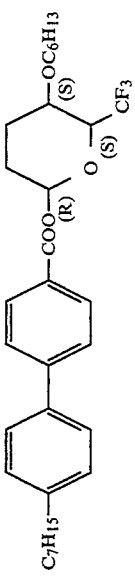 | 44 61 66 | 55 | −7.1 | −19 | 17 |
Respone time: V = ±5V/μm, 30° C., 0→50% Change in transmittance

TABLE 2

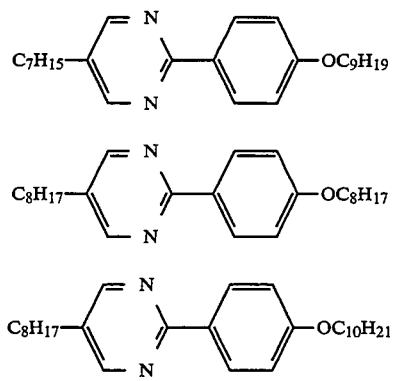

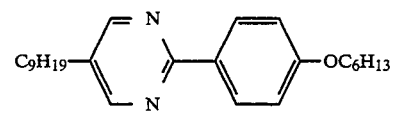

Transition temperature of each 25 wt % composition $S_C$ 50 $S_A$ 62 N 68 I

Next, liquid crystal mixtures LC1 to LC5 shown in Table 4 were prepared using liquid crystalline compounds represented by Formula I II shown in Table 3. The transition temperature of the liquid crystal mixtures LC1 to LC5 are shown in Table 5.

TABLE 3

| Compound No. | Structural formula | Transition temperature (°C.) |
|---|---|---|
| FA-050 | $C_8H_{17}O$—◯—◯—◯—COO—◯—COO$C_7H_{15}$ | K 79 Sx 92 Sc 113 Sa 194 I |
| FA-067 | $C_8H_{17}O$—◯(F,F)—COO—◯—$OC_{10}H_{21}$ | K 56 Sc 75 N 83 I |
| FA-068 | $C_8H_{17}O$—◯(F,F)—COO—◯—$OC_8H_{17}$ | K 49 Sc 71 N 81 I |
| FA-069 | $C_8H_{17}O$—◯(F,F)—COO—◯—pyrimidine—$OC_8H_{17}$ | K 81 Sc 129 N 174 I |
| FA-075 | $C_8H_{17}O$—naphthyl—◯(F,F)—$C_8H_{17}$ | K 58 (Sc 40) Sa 77 N 79 I |
| FA-076 | $C_8H_{17}$—cyclohexyl—◯—◯(F,F)—$C_8H_{17}$ | K 53 Sa 105 I |
| FA-077 | $C_8H_{17}O$—naphthyl—◯(F,F)—$OC_{10}H_{21}$ | K 68 Sc 99 Sa 102 N 106 I |

TABLE 3-continued

| Compound No. | Structural formula | Transition temperature (°C.) |
|---|---|---|
| FB-022 | C₁₀H₂₁—[phenyl]—[phenyl(F)]—OC₈H₁₇ | K 40 Sc 52 Sa 61 N 65 I |
| FB-029 | C₈H₁₇O—[phenyl(F)]—[phenyl]—[phenyl(F)]—C₈H₁₇ | K 60 Sc 109 Sa 128 I |
| FB-021 | C₈H₁₇O—[phenyl]—[phenyl(F)]—OC₈H₁₇ | K 51 (Sc 40) N 63 I |
| FB-038 | C₅H₁₁O—[phenyl(F)]—[phenyl(F)]—[phenyl]—C₈H₁₇ | K 63 Sc 93 Sa 126 N 127 I |
| FA-083 | C₆H₁₃O—[naphthyl]—[phenyl(F,F)]—C₈H₁₇ | K 54 (Sc 44) Sa 66 N 77 I |
| FA-081 | C₁₀H₂₁O—[naphthyl]—[phenyl(F,F)]—C₈H₁₇ | K 51 (Sc 39) Sa 81 I |
| FA-087 | CH₃—CH(CH₃)—(CH₂)₃—O—[naphthyl]—[phenyl(F,F)]—C₈H₁₇ | K 54 (Sc 45 Sa 46) N 56 I |
| FA-078 | C₈H₁₇—[cyclohexyl]—[phenyl]—[phenyl(F,F)]—OC₁₀H₂₁ | K 62 (Sc 51) Sa 128 I |
| FA-090 | C₈H₁₇O—[phenyl]—[phenyl(F,F)]—OC₁₀H₂₁ | K 57 Sc 60 Sa 61 N 62 I |

TABLE 4

|  | LC1 | LC2 | LC3 | LC4 | LC5 |
|---|---|---|---|---|---|
| FA-050 | 5.6% | | | | |
| FA-067 | 16.1% | | | | 10.0% |
| FA-068 | 16.5% | | | | 10.0% |
| FA-069 | 5.3% | | | | |
| FA-075 | 12.3% | 12.5% | 10.0% | 15.0% | 10.0% |
| FA-076 | 16.5% | | | | |
| FA-077 | 5.0% | | | | |
| FA-078 | | | 10.0% | | |
| FA-081 | | 12.5% | 10.0% | 15.0% | 10.0% |
| FA-083 | | 12.5% | 10.0% | 15.0% | 10.0% |
| FA-087 | | 12.5% | 10.0% | 15.0% | 10.0% |
| FA-090 | | | 10.0% | | |
| FB-021 | | 12.5% | 10.0% | 10.0% | 10.0% |
| FB-022 | 11.3% | 12.5% | 10.0% | 10.0% | 10.0% |
| FB-029 | 11.4% | 12.5% | 10.0% | 10.0% | 10.0% |
| FB-038 | | 12.5% | 10.0% | 10.0% | 10.0% |

TABLE 5

|  | K |  | $S_C$ |  | $S_A$ |  | N |  | I |
|---|---|---|---|---|---|---|---|---|---|
| LC1 | . | <RT | . | 77 | . | 84 | . | 95 | . |
| LC2 | . | <0 | . | 59 | . | 78 | . | 82 | . |
| LC3 | . | <0 | . | 60 | . | 78 | . | 83 | . |
| LC4 | . | <0 | . | 57 | . | 74 | . | 79 | . |
| LC5 | . | <0 | . | 66 | . | 68 | . | 81 | . |

The ferroelectric liquid crystal mixtures FLC1 to FLC5 shown in Table 6 were prepared using the liquid crystal mixtures LC1 to LC5 and the chiral compounds shown in Table 1. The transition temperature of the ferroelectric liquid crystal mixtures FLC1 to FLC5 are shown in Table 7.

TABLE 6

| FLC1 | | FLC2 | | FLC3 | | FLC4 | | FLC5 | |
|---|---|---|---|---|---|---|---|---|---|
| LC1 | 98.0% | LC2 | 99.0% | LC3 | 99.0% | LC4 | 99.0% | LC5 | 99.0% |
| KLC340RA | 0.6% | KLC340RA | 0.2% | KLC340RA | 0.2% | KLC340RA | 0.3% | KLC340RA | 0.3% |
| KLC372RA | 1.4% | KLC375SA | 0.8% | KLC375SA | 0.8% | KLC375SB | 0.7% | KLC375SB | 0.7% |

TABLE 7

|  | K |  | $S_C*$ |  | $S_A$ |  | N* |  | I |
|---|---|---|---|---|---|---|---|---|---|
| FLC1 | . | <RT | . | 76 | . | 84 | . | 94 | . |
| FLC2 | . | <0 | . | 57 | . | 75 | . | 80 | . |
| FLC3 | . | <0 | . | 56 | . | 77 | . | 82 | . |
| FLC4 | . | <RT | . | 53 | . | 73 | . | 78 | . |

TABLE 7-continued

|  | K |  | $S_C*$ |  | $S_A$ |  | N* |  | I |
|---|---|---|---|---|---|---|---|---|---|
| FLC5 | . | <RT | . | 64 | . | 68 | . | 79 | . |

Examples 6 to 8

Ferroelectric liquid crystal mixtures FLC6 to FLC8 were prepared. In each of these examples, a ferroelectric liquid crystal mixture was prepared by adding the achiral compound represented by Formula I or II to a known ferroelectric liquid crystal mixture.

As the known ferroelectric liquid crystal mixture, ferroelectric liquid crystal mixture SCE8 manufactured by Merck & Co., Inc. was used. The achiral compounds (racemic bodies) represented by Formulae I and II shown in Table 8 were obtained in accordance with Synthesis Examples. The racemic bodies shown in Table 8 were respectively added to SCE8 to prepare the ferroelectric liquid crystal mixtures FLC6 to FLC8 shown in Table 9. The transition temperature of the ferroelectric liquid crystal mixtures FLC6 to FLC8 are shown in Table 10.

TABLE 8

Structural formula

KLC334NA
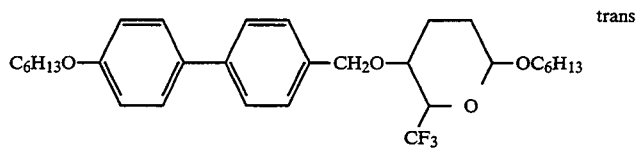
trans

KLC403NA
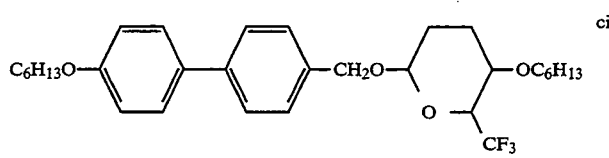
cis

KLC451NA
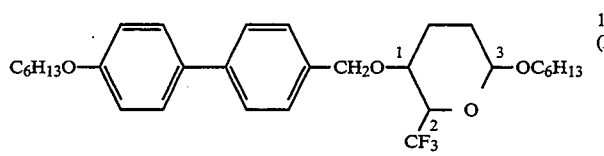
1,2,3 (R,S,R) and (S,R,S)

TABLE 9

|  | FLC6 | FLC7 | FLC8 |
|---|---|---|---|
| SCE8 | 90.0% | 90.0% | 90.0% |
| KLC334NA | 10.0% | | |
| KLC403NA | | 10.0% | |
| KLC451NA | | | 10.0% |

TABLE 10

|  | K |  | $S_C*$ |  | $S_A$ |  | N* |  | I |
|---|---|---|---|---|---|---|---|---|---|
| FLC6 | . | <RT | . | 46 | . | 68 | . | 93 | . |
| FLC7 | . | <RT | . | 44 | . | 73 | . | 92 | . |
| FLC8 | . | <RT | . | 49 | . | 63 | . | 92 | . |

Example 9

A liquid crystal device of the present invention will be described.

Figure 4:
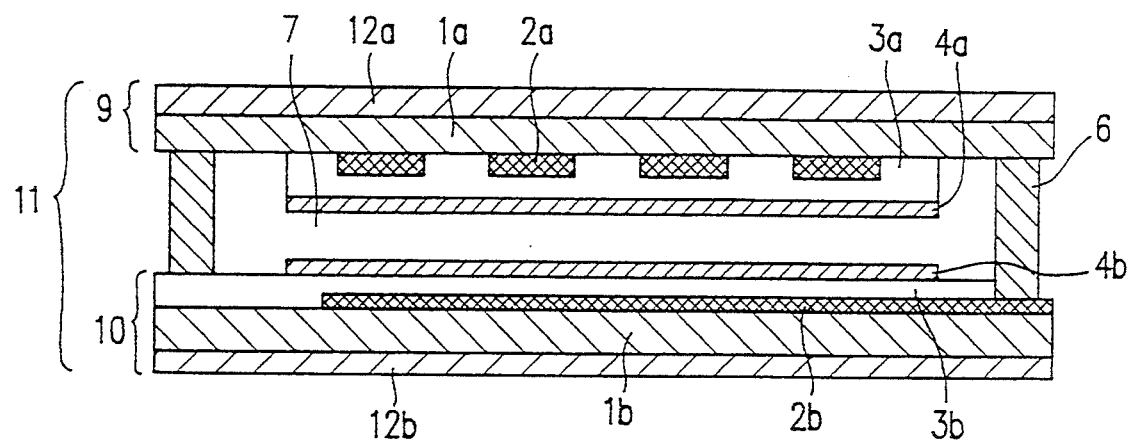
FIG. 4 is a cross-sectional view of a ferroelectric liquid crystal device of the present invention.

FIG. 4 is a cross-sectional view of a transmission type liquid crystal device using the ferroelectric liquid crystal mixture of the present invention. The liquid crystal device shown in FIG. 4 includes insulating substrates 1a, 1b, transparent electrodes 2a, 2b, insulating films 3a, 3b, alignment films 4a, 4b, a sealant 6, ferroelectric liquid crystal 7, and polarizing plates 12a, 12b. As the insulating substrates 1a, 1b, transparent substrates such as glass substrates are generally used. The transparent electrodes 2a, 2b having a predetermined pattern, made of a conductive thin film such as $InO_3$, $SnO_2$, and Indium-Tin Oxide (ITO) are respectively formed on the insulating substrates 1a, 1b. On the transparent electrodes 2a, 2b, the insulating films 3a, 3b are generally formed. It is not necessary that the insulating films 3a, 3b are formed thereon. As the insulating films 3a, 3b, an inorganic thin film such as $SiO_2$, SiNx, and $Al_2O_3$, and an organic thin film such as polyimide, photoresist resin, and polymer liquid crystal can be used. The inorganic thin film can be formed by vacuum evaporation, sputtering, chemical vapor deposition (CVD), or solution coating. The organic thin film can be formed by coating a solution of an organic substance by spinner coating, dip coating, screen printing, roller coating, or the like and curing the solution if required. The organic thin film can also be formed by vacuum evaporation, sputtering, CVD, Langumuir-Blodgett (LB) or the like.

The alignment films 4a, 4b are formed on the insulating films 3a, 3b. In the case where the insulating films 3a, 3b are not formed, the alignment films 4a, 4b are directly formed on the transparent electrodes 2a, 2b. As the alignment films 4a, 4b, an inorganic film or an organic film can be used. A silicon oxide film which is oblique-deposited by evaporation is often used as the alignment film of an inorganic type. A silicon oxide film which is rotation-deposited by evaporation can also be used. Alternatively, a thin film of $SiO_2$, SiNx or the like is formed by vacuum evaporation, sputtering, CVD, or the like, and the surface of the resulting film is rubbed to form an alignment film. Nylon, polyvinyl alcohol, polyimide, and the like can be used as the organic alignment film. In general, the surface of such an organic film is rubbed to form an alignment film. In addition, a polymer liquid crystal film and an LB film can be used as the alignment film. Furthermore, liquid crystal can be oriented using a magnetic field or by a spacer edge method. Two insulating substrates on which the alignment films are formed are attached to each other, and then ferroelectric liquid crystal is injected therebetween to obtain the ferroelectric liquid crystal device of the present invention.

Next, the preferred orientation of the ferroelectric liquid crystal in the liquid crystal device of the present invention will be described.

As described above, various methods can be used for the alignment of liquid crystal in the ferroelectric liquid crystal device. Among them, the method which is most excellent in mass-production is a rubbing method. There are mainly three kinds of rubbing methods: parallel rubbing, antiparallel rubbing, and rubbing of only one substrate. According to parallel rubbing, upper and lower substrates are rubbed and the respective rubbing directions are parallel. According to antiparallel rubbing, upper and lower substrates are rubbed, and the respective rubbing directions are antiparallel with each other. According to the rubbing of only one substrate, only one of upper and lower substrates is rubbed.

The rubbing of only one substrate has a disadvantage that it is difficult to obtain satisfactorily uniform orientation. The reason for this is as follows: A ferroelectric liquid crystal material is optically active liquid crystal. When the ferroelectric liquid crystal material exhibits a nematic phase on a higher temperature side, the nematic phase has a helical structure, leading to the difficulty of obtaining uniform orientation. If the ferroelectric liquid crystal material does not exhibit a nematic phase on a higher temperature side, such a problem is not caused. However, in this case, an isotropic liquid state is directly changed to a smectic phase. Thus, it is also difficult to obtain satisfactorily uniform orientation.

In the case of the antiparallel rubbing, linear defects are likely to be caused along the rubbing direction. Thus, it is also difficult to obtain uniform orientation. The most effective method for obtaining uniform orientation is that a ferroelectric liquid crystal material having an INAC phase sequence is used in a parallel rubbing cell. In this case, although a helical structure is present in a nematic phase, the orientation of molecules are regulated by both sides of the upper and lower substrates. Therefore, uniform orientation is likely to be obtained in a nematic phase, and when the temperature of the cell is decreased so as to obtain a phase sequence of a chiral nematic phase, a smectic A phase, and a chiral smectic C phase, the orientation along the rubbing direction of the cell can be easily obtained.

Figure 5A:
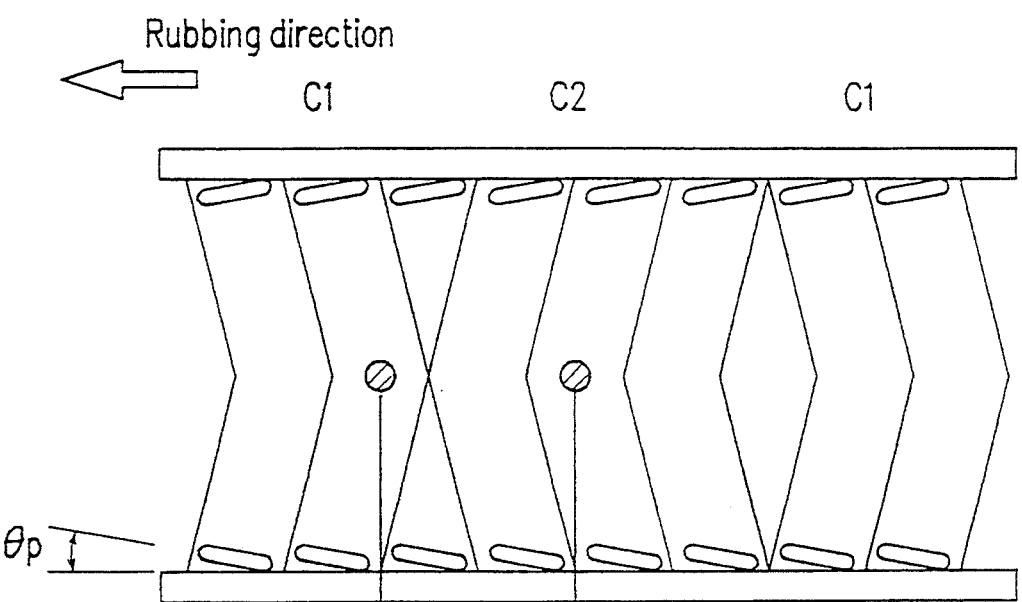
FIGS. 5A and 5B are model diagrams showing C1 and C2 orientations in the ferroelectric liquid crystal device of the present invention.
Figure 5B:
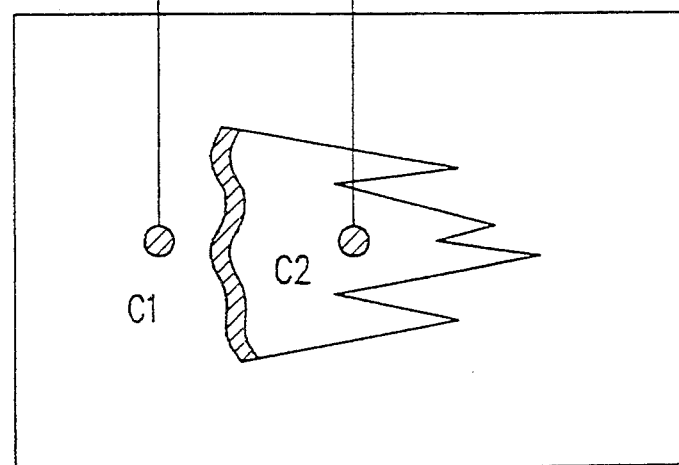
Figure 6:
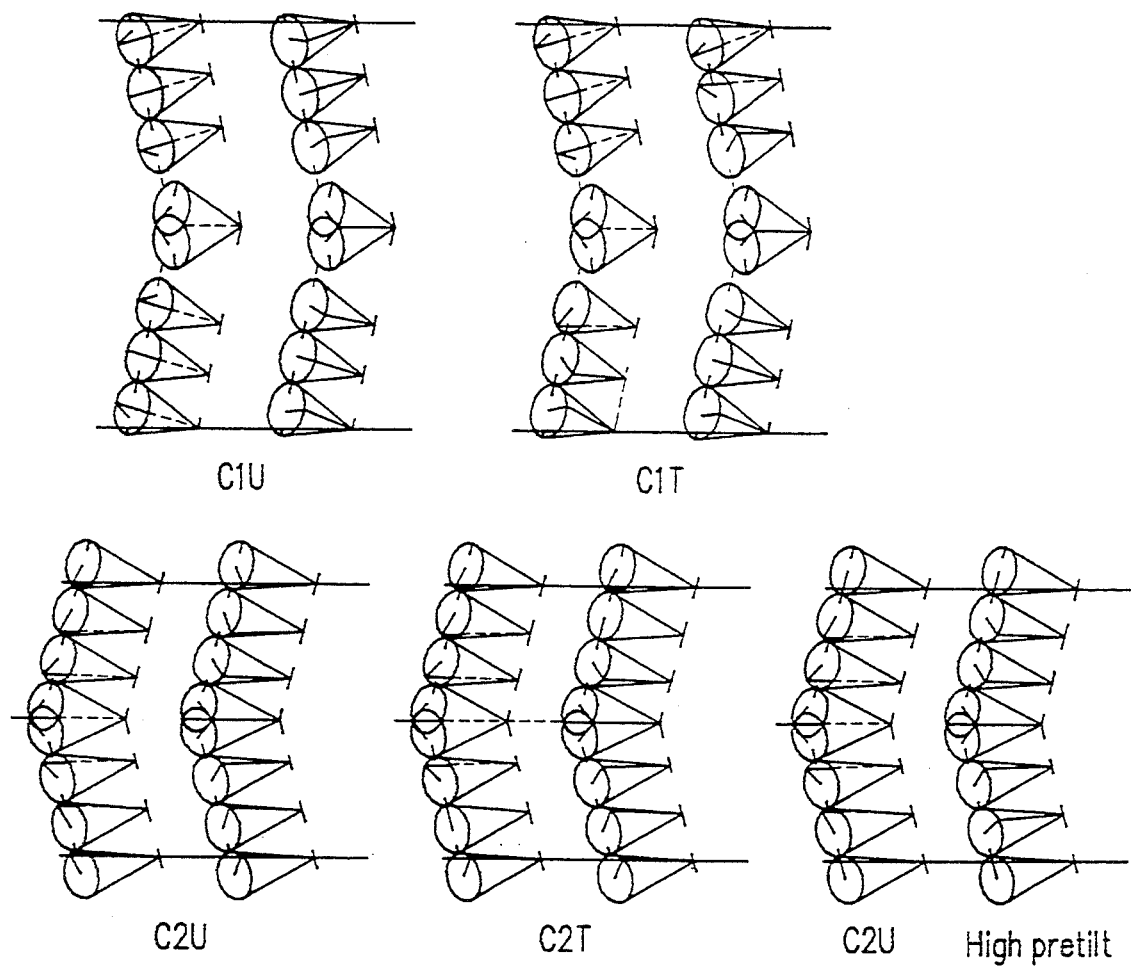
FIG. 6 shows models of four molecular orientations of ferroelectric liquid crystal.

However, in the ferroelectric liquid crystal device using parallel rubbing, the orientation in the chiral smectic C phase is not limited to one. There are two reasons why uniform orientation cannot be obtained over the entire surface of the substrates. One of the reasons is concerned with the bend of a smectic layer. It is well known that the ferroelectric liquid crystal has a bent layer structure (i.e., chevron structure). As shown in FIG. 5, in the chevron structure, there are two regions. Kanbe et al. call these regions C1 and C2, considering the relationship with a pretilt angle. The other reason is concerned with uniformity (U) and twist (T). Uniformity refers to orientation showing an extinction direction and twist refers to orientation showing no extinction direction. Koden et al. has reported that in the ferroelectric liquid crystal cell of parallel rubbing using a high pretilt alignment film, three orientations such as C1U (C1-uniform), C1T (C1-twist), and C2 are obtained. See M. Koden et al., Jpn. J. Appl. phys., 30, L1823 (1991). The inventors of the present invention have further studied the orientation of the ferroelectric liquid crystal cell with parallel rubbing; as a result, it was found that in the ferroelectric liquid crystal cell using parallel rubbing, four orientations such as C1U, C1T, C2U, and C2T are present. FIG. 6 shows these four orientations.

The comparison among four orientations obtained in the ferroelectric liquid crystal cell having negative dielectric anisotropy is as follows:

In C1T and C2T, the extinction direction is not present and a black state is not sufficiently black, so that a satisfactory contrast cannot be obtained. C1U is difficult to be switched, and even though it is switched, C1U is changed to any orientation in which C2 is mixed during driving. In contrast, the inventors of the present invention has found that C2U provides a satisfactory contrast.

The occurrence of C1 and C2 is related to a pretilt angle. When the pretilt angle is in the range of 0° to 15°, C2 will occur. As reported by Koden et al., when the pretilt angle is high, C2 occurs as only one state (i.e., C2U) showing the extinction direction, which is rather preferred. When the pretilt angle is too high, C1 rather than C2 is likely to occur, so that the pretilt angle is preferably 10° or less. On the other hand, when the pretilt angle is too low, C2T easily occurs. Accordingly, the pretilt angle is preferably in the range of 5° to 10° so as to obtain C2U.

Next, a method for driving will be described.

Figure 2:
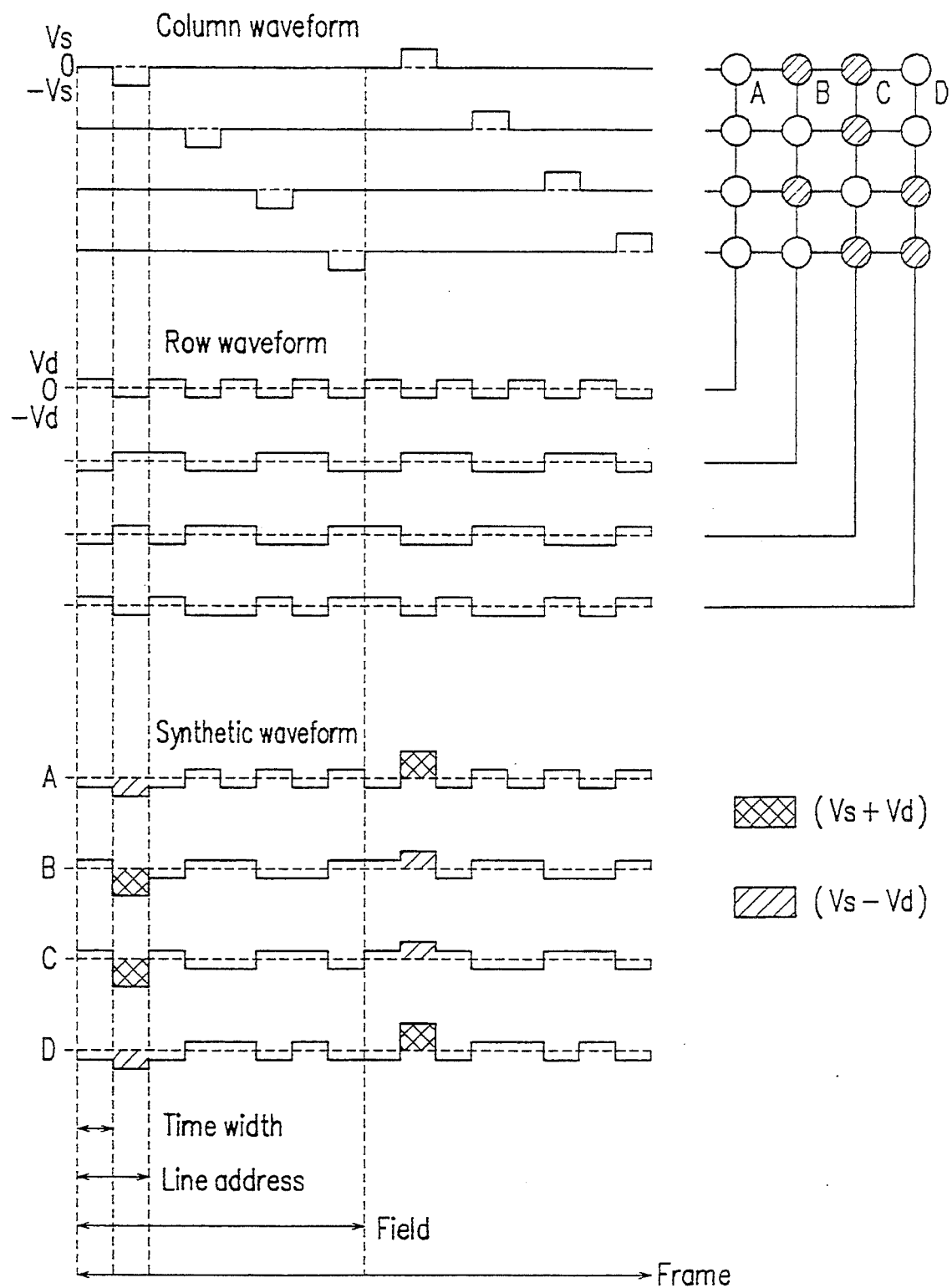
FIG. 2 is a timing chart showing an example of driving waveforms used for driving the ferroelectric liquid crystal device having the $\tau$-V characteristic of FIG. 1B.
Figure 7:
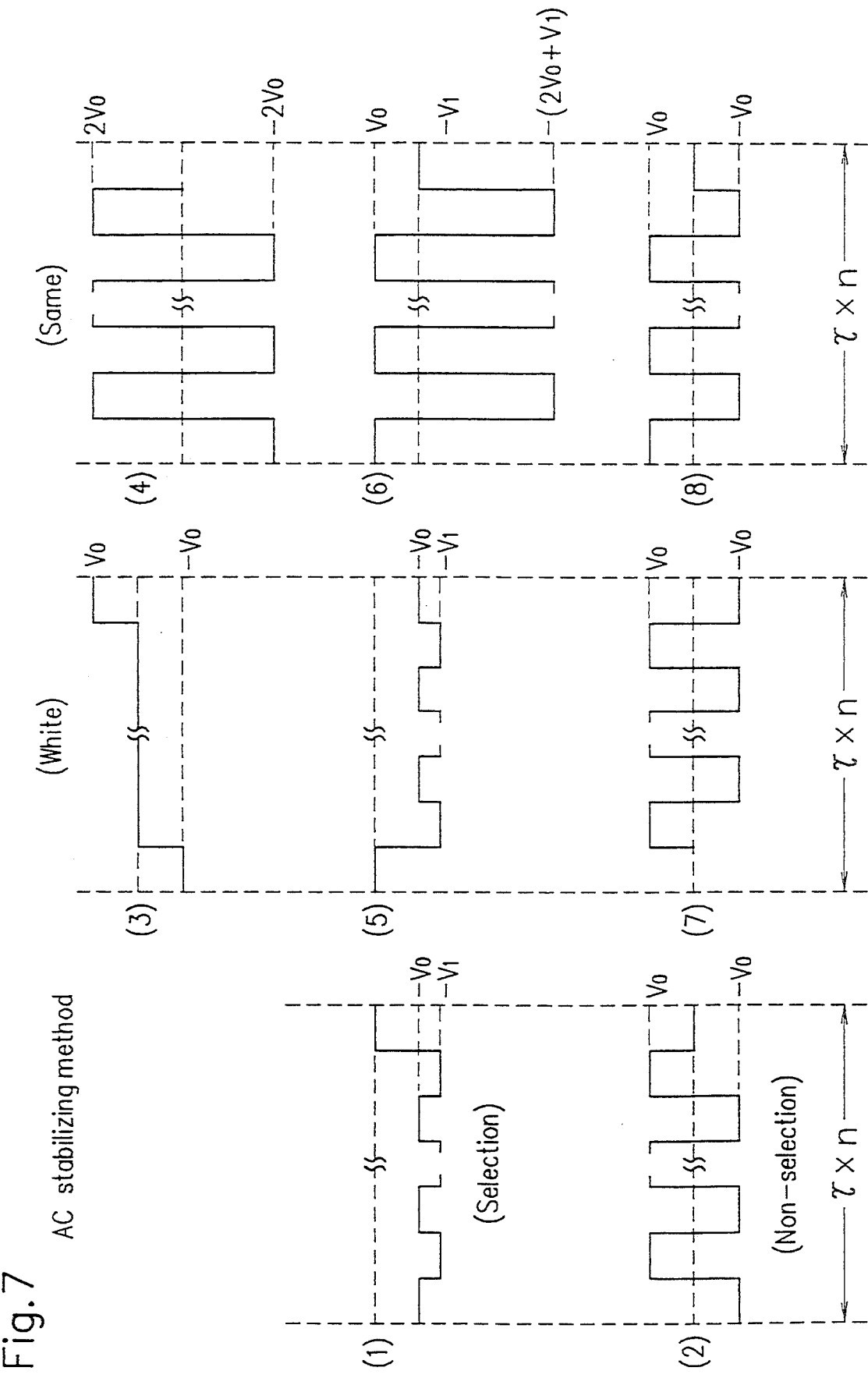
FIG. 7 is a timing chart showing an example of driving waveforms used for driving the ferroelectric liquid crystal device having the $\tau$-V characteristic of FIG. 1B.

The method for driving shown in FIG. 2 can be used; A more preferred method for driving is shown in FIG. 7. The method shown in FIG. 7 is capable of partially rewriting. This driving method is preferred for realizing a display of large capacity such as 2000×2000 lines, using the ferroelectric liquid crystal device. According to this driving method, a driving voltage having a waveform (1) is applied to scanning electrodes connected to pixels to be rewritten, and a driving voltage having a waveform (2) is applied to the other scanning electrodes. A driving voltage having a waveform (4) is applied to signal electrodes connected to pixels which are not to be rewritten. In FIG. 7, the same waveform is repeated (n-1)/2 times; however, the repetition time can be appropriately set at one or more. It is possible that driving voltages having waveforms (5) to (8) are set so that the intensity of transmitted light obtained when these driving voltages are applied to pixels are almost equal. Thus, a satisfactory display without flickering can be realized.

In the present specification, specific driving methods, parallel rubbing and C2-uniform orientation are exemplified as a preferred embodiment using the ferroelectric liquid crystal mixture of the present invention. It is noted that the present invention is not limited thereto. It is understood by those skilled in the art that other types of ferroelectric liquid crystal devices and methods for driving the same can be used.

Example 9

An ITO film and an $SiO_2$ film were formed in this order on two glass substrates, respectively. Then, a polyimide film was coated onto the respective $SiO_2$ films and rubbed. The two glass substrates were attached to each other so that the respective rubbing directions were identical and the cell thickness was 2 μm. Thus, eight pairs of liquid crystal cells were obtained. The ferroelectric liquid crystal mixtures FLC1 to FLC8 prepared in Examples 1 to 8 were injected into the respective cells. After injection, each cell was heated to a temperature at which the liquid crystal mixture was changed to an isotropic phase. Then, each cell was cooled to room temperature at 1° C/min., whereby ferroelectric liquid crystal devices having satisfactory orientation were obtained.

Figure 8:
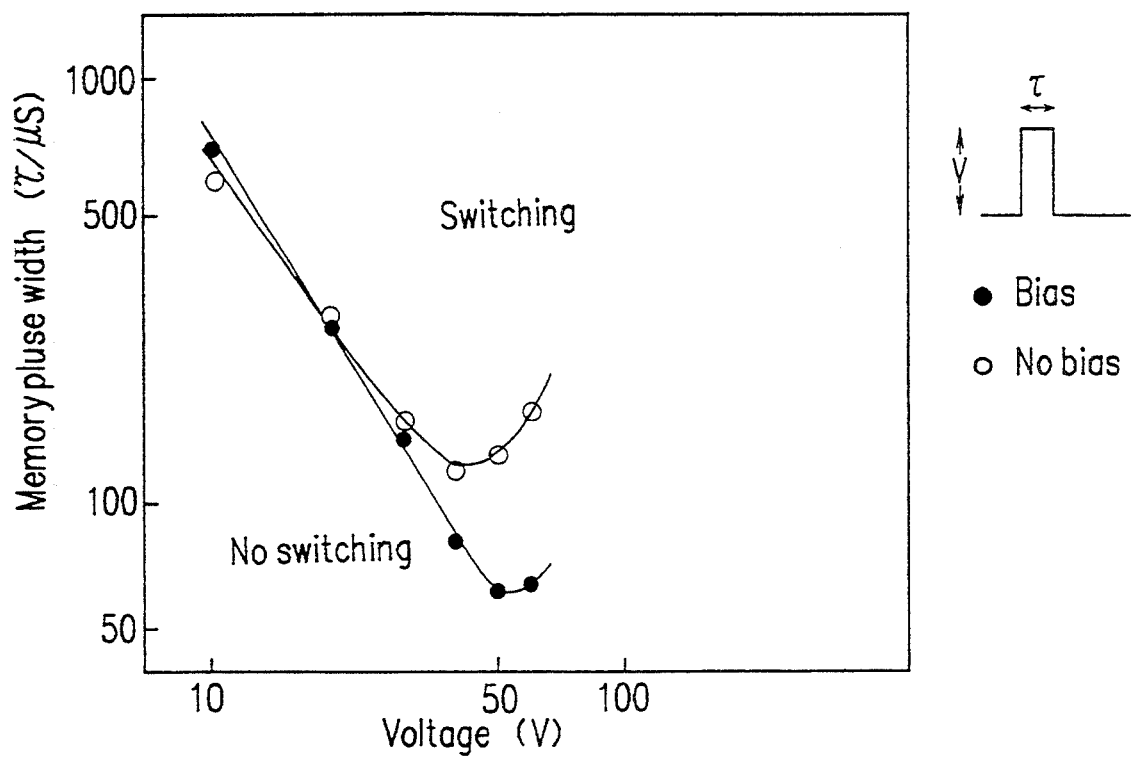
FIG. 8 is a graph showing a $\tau$-V characteristic of the ferroelectric liquid crystal device of the present invention.
Figure 9:
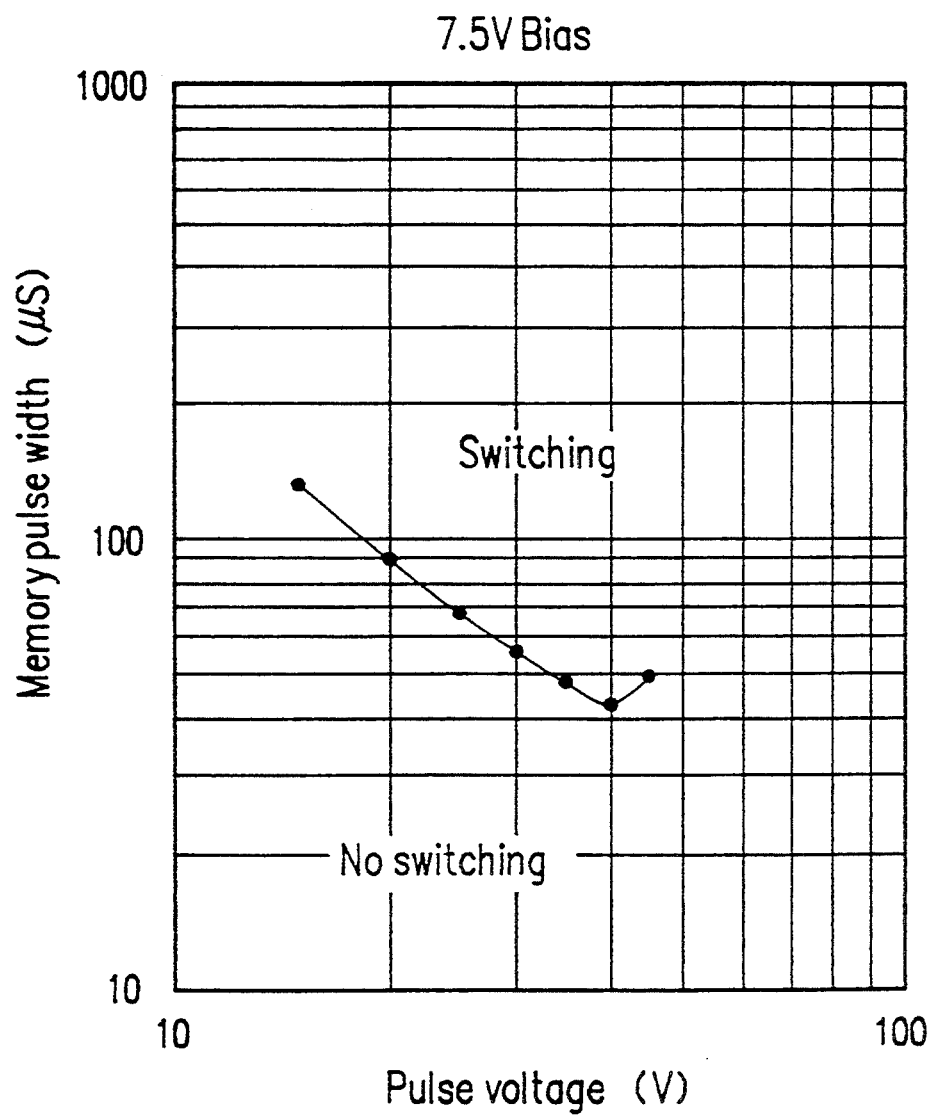
FIG. 9 is a graph showing a $\tau$-V characteristic in the case where a bias is applied to another ferroelectric liquid crystal device of the present invention.
Figure 10:
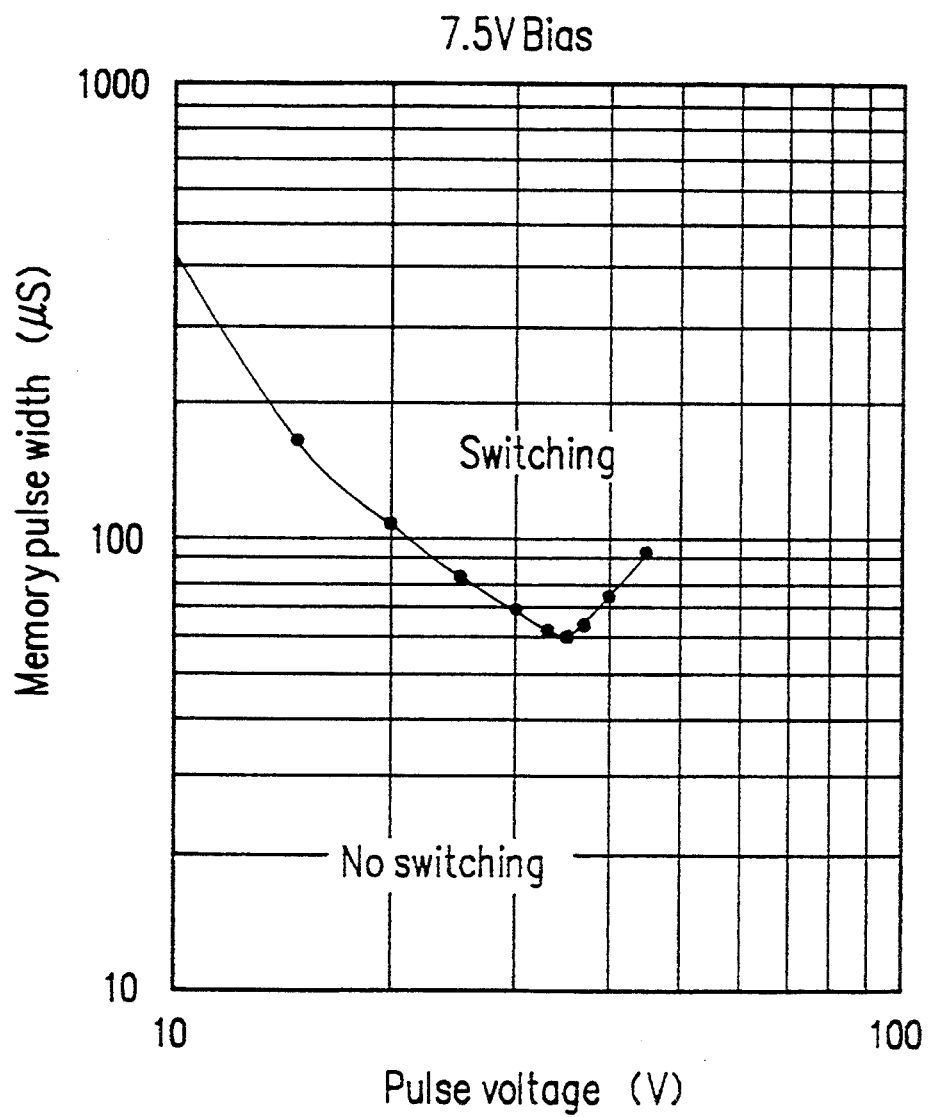
FIG. 10 is a graph showing a τ-V characteristic in the case where a bias is applied to still another ferroelectric liquid crystal device of the present invention.
Figure 11:
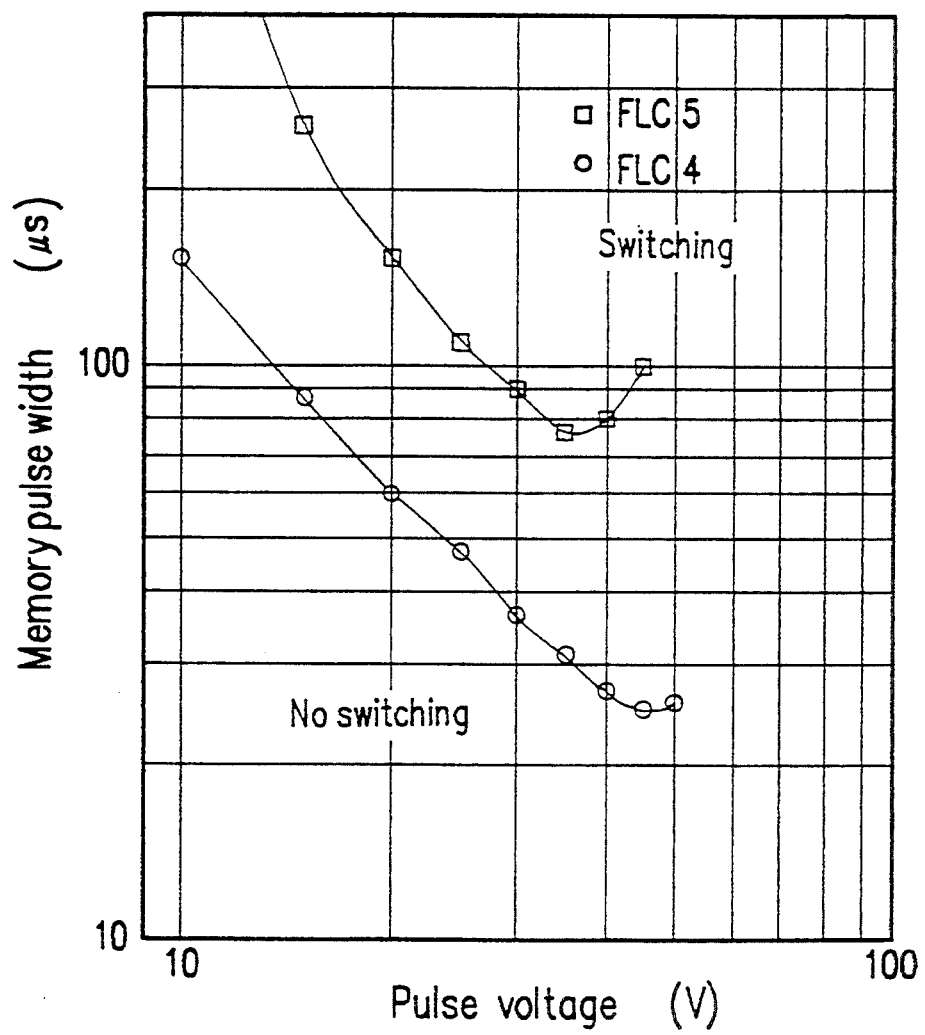
FIG. 11 is a graph showing τ-V characteristics in the case where a bias is applied to the other two ferroelectric liquid crystal devices of the present invention.
Figure 12:
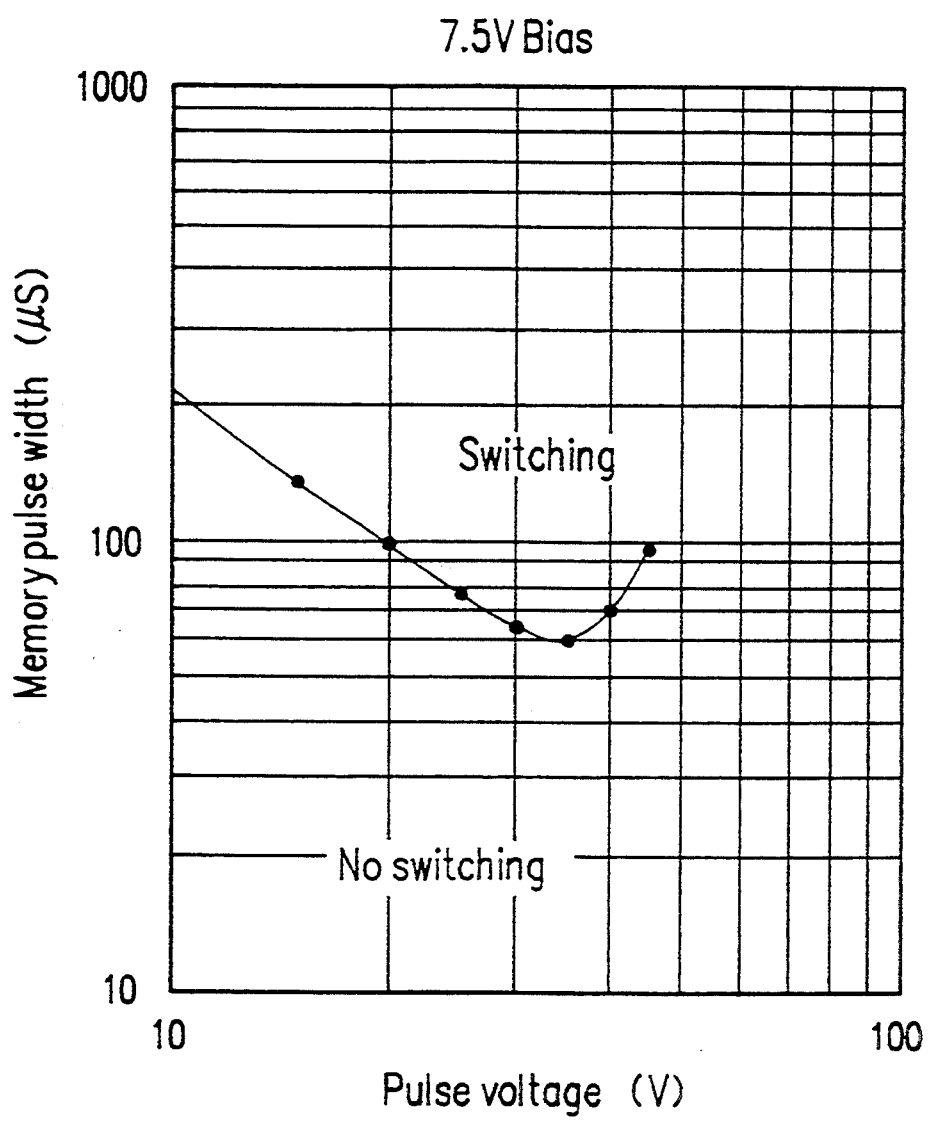
FIG. 12 is a graph showing a τ-V characteristic in the case where a bias is applied to still another ferroelectric liquid crystal device of the present invention.
Figure 13:
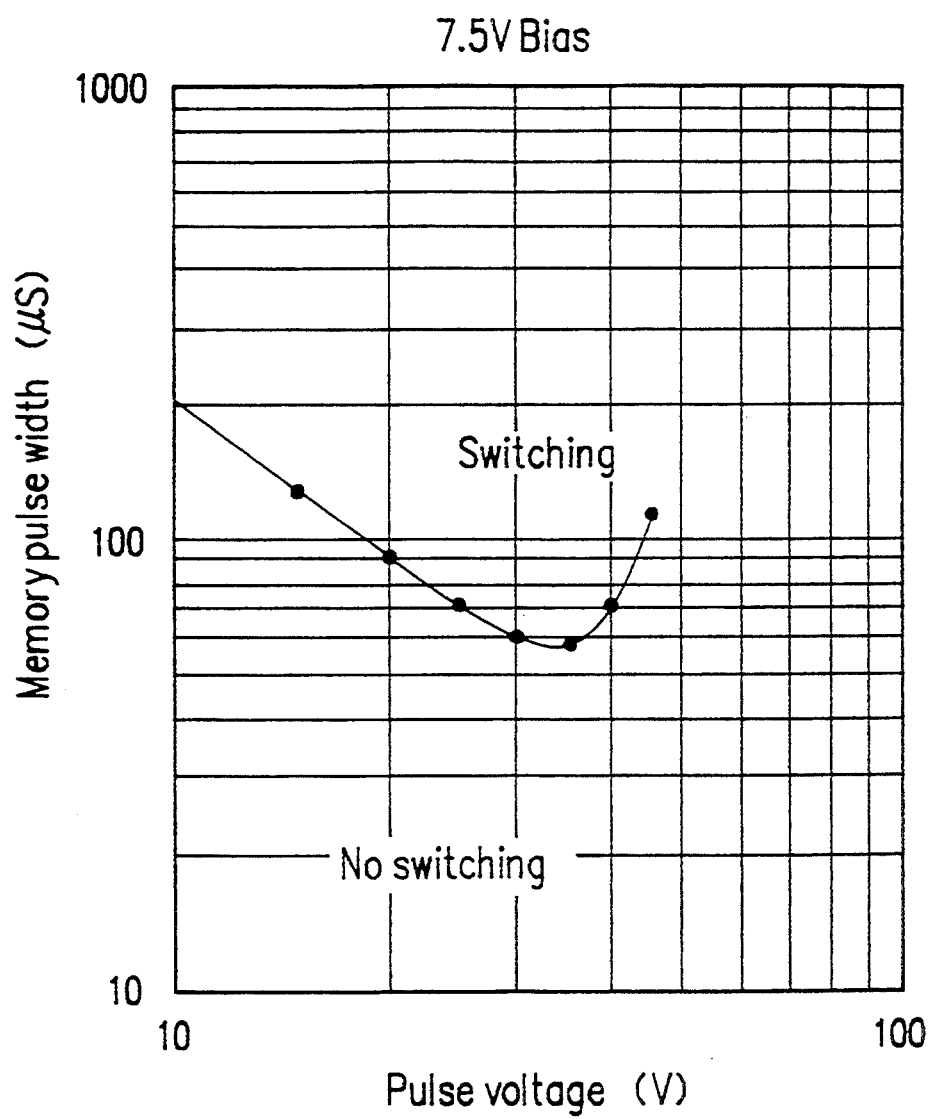
FIG. 13 is a graph showing a τ-V characteristic in the case where a bias is applied to still another ferroelectric liquid crystal device of the present invention.
Figure 14:
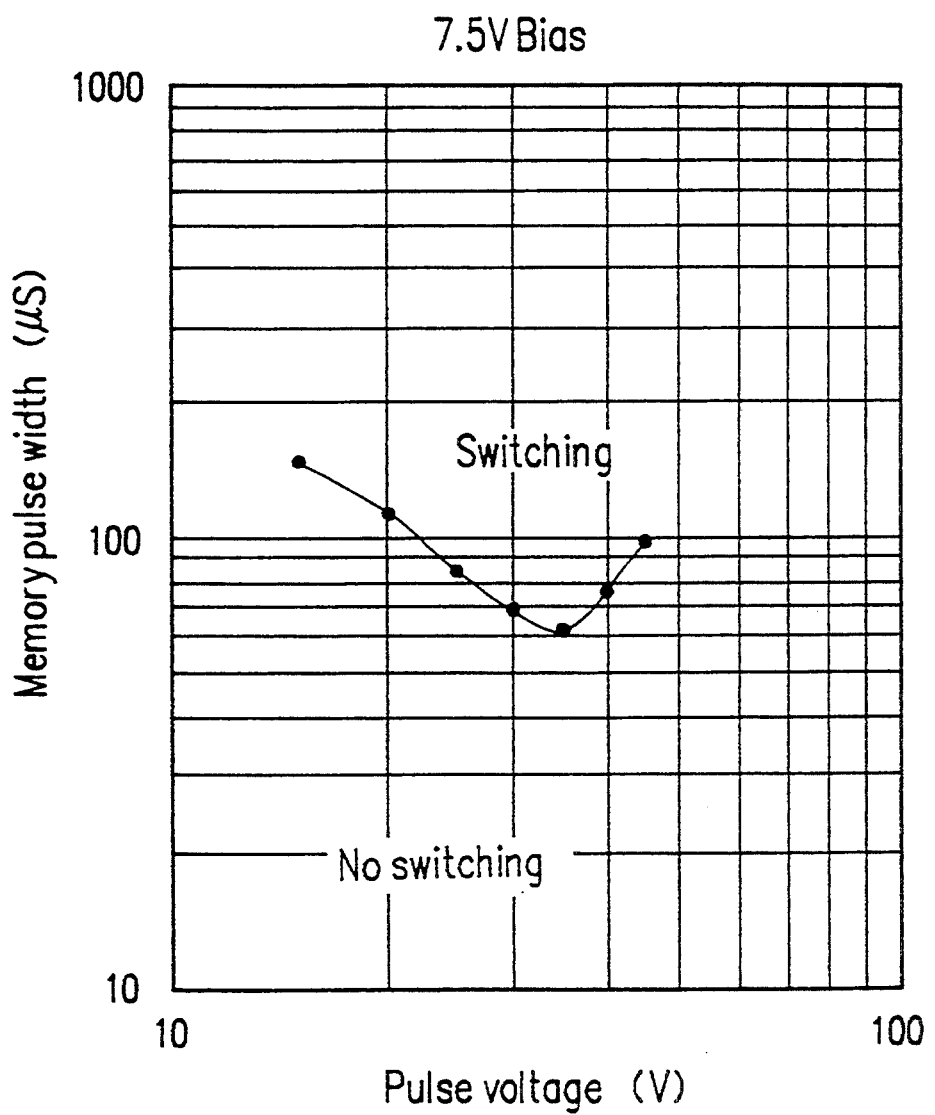
FIG. 14 is a graph showing a τ-V characteristic in the case where a bias is applied to still another ferroelectric liquid crystal device of the present invention.

Each ferroelectric liquid crystal device was placed between two polarizers orthogonal to each other. Each device was evaluated for the relation ($\tau - V_{min}$ characteristic) between a pulse width (memory pulse width) required for memory and a voltage. The results obtained with respect to FLC1 to FLC3 are shown in FIGS. 8 to 10; those obtained with respect to FLC4 and FLC5 are shown in FIG. 11; and those obtained with respect to FLC6 to FLC8 are shown in FIGS. 12 to 14. In any of these figures, $V_{min}$ can be recognized.

Example 10

A driving test was conducted in the ferroelectric liquid crystal devices fabricated in Example 9, using driving waveforms shown in FIG. 7. Driving conditions and results of the driving test are shown in Table 11. As is understood from the results, the devices can be switched by a driving voltage of 40 V or less and a contrast ratio of 20:1 or more can be obtained. The angle between two memory states during driving was 47°; thus, a bright display was obtained.

TABLE 11

| Liquid crystal material | Measurement temperature | Line address time μsec | Pulse width μsec | $V_1$ Rewrite V | $V_1 + 2V_0$ Non-rewrite V | $V_0$ Bias V | Repetition time | 2θm deg | CR |
|---|---|---|---|---|---|---|---|---|---|
| FLC1 | 25° C. | 600 | 20 | 12.0 | 40.0 | 14.0 | 7 | 47 | >20 |
| FLC2 | 25° C. | 414 | 23 | 26.0 | 40.0 | 7.0 | 4 | 19 | >20 |
| FLC3 | 30° C. | 196 | 14 | 32.0 | 40.0 | 4.0 | 3 | 15 | >20 |
| FLC6 | 25° C. | 450 | 25 | 26.0 | 40.0 | 7.0 | 4 | 16 | >20 |
| FLC7 | 25° C. | 360 | 20 | 27.0 | 40.0 | 6.5 | 4 | 15 | >20 |
| FLC8 | 25° C. | 504 | 28 | 26.0 | 40.0 | 7.0 | 4 | 17 | >20 |

Example 11

A driving test was conducted in the ferroelectric liquid crystal devices fabricated in Example 9, using driving waveforms shown in FIG. 2. Driving conditions and results of the driving test are shown in Table 12. As is understood from the results, the devices can be switched by a driving voltage of 40 V or less and a contrast ratio of 20:1 or more can be obtained.

TABLE 12

| Liquid crystal material | Measurement temperature | Line address time μsec | Pulse width μsec | $V_1$ Rewrite V | $V_1 + 2V_0$ Non-rewrite V | $V_0$ Bias V | 2θm deg | CR |
|---|---|---|---|---|---|---|---|---|
| FLC3 | 30° C. | 148 | 37 | 32.0 | 40.0 | 4.0 | 15 | >20 |
| FLC6 | 25° C. | 392 | 98 | 26.0 | 40.0 | 7.0 | 16 | >20 |
| FLC7 | 25° C. | 292 | 73 | 28.0 | 40.0 | 6.0 | 14 | >20 |

Example 12

Figure 15:
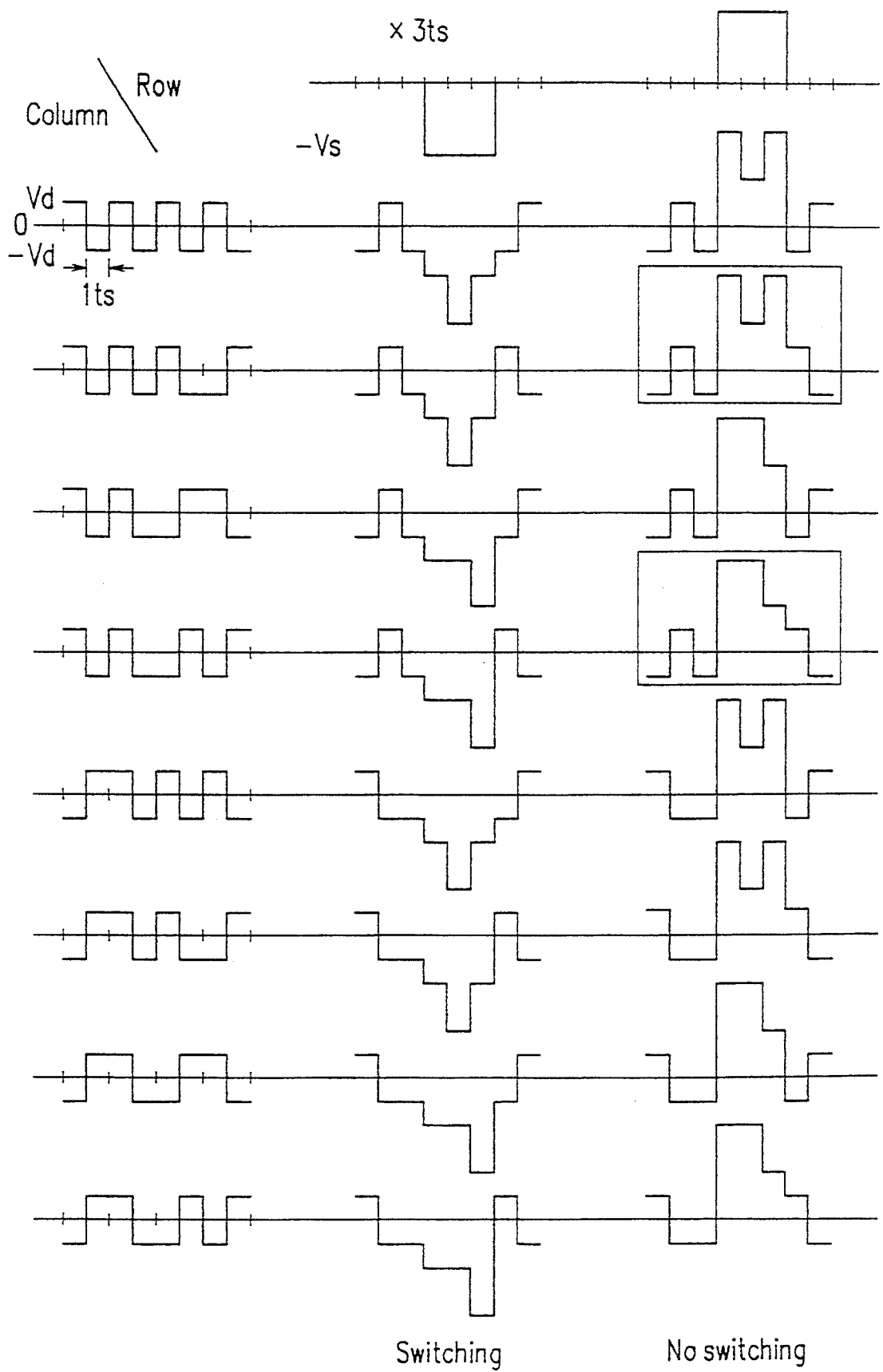
FIG. 15 shows an example of driving waveforms for driving a ferroelectric liquid crystal device using a τ-$V_{min}$ characteristic.

A driving test was conducted in the ferroelectric liquid crystal devices fabricated in Example 9, using driving waveforms shown in FIG. 15. Driving conditions and results of the driving test are shown in Table 13. As is understood from the results, the devices can be switched by a driving voltage of 40 V or less and a contrast ratio of 20:1 or more can be obtained.

TABLE 13

| Liquid crystal material | Measurement temperature | Line address time μsec | Pulse width μsec | V₁ Rewrite V | V₁ + 2Vo Non-rewrite V | Vo Bias V | 2θm deg | CR |
|---|---|---|---|---|---|---|---|---|
| FLC3 | 30° C. | 52 | 13 | 30.0 | 40.0 | 5.0 | 16 | >20 |

As described above, according to the present invention, the ferroelectric liquid crystal device has ferroelectric liquid crystal sandwiched between a pair of insulating substrates, each having at least an electrode film and an alignment film. The device includes a driving unit for switching an optical axis of liquid crystal by selectively applying a voltage to the electrode and a unit for optically identifying the optical axis. The ferroelectric liquid crystal is the above-mentioned liquid crystal mixture.

Furthermore, the electrodes of the liquid crystal device are arranged so as to cross each other, whereby a plurality of scanning electrodes and a plurality of signal electrodes are formed. Each crossed region of the scanning electrodes and the signal electrodes forms a pixel. It is preferred that a positive voltage pulse or a negative voltage pulse lower than a local minimum value $V_{min}$ is applied to a pixel composed of a scanning electrode to which a non-selection voltage is applied and a signal electrode to which a rewrite voltage is applied; A positive voltage pulse or a negative voltage pulse higher than the local minimum value $V_{min}$ and a negative voltage or a positive voltage lower than the local minimum value $V_{min}$ are applied to a pixel composed of a scanning electrode to which a selection voltage is applied and a signal electrode to which a holding voltage is applied; and a positive voltage pulse (or a negative voltage pulse) suitable for switching (i.e., a voltage pulse in the vicinity of the local minimum value $V_{min}$ in the voltage-pulse width characteristic) is applied to a pixel composed of a scanning electrode to which a selection voltage is applied and a signal electrode to which a rewrite voltage is applied.

As a method for driving, those disclosed in P. W. H. Surguy et al., Ferroelectrics., 122, 63(1991); J. R. Hughes et al., WO92/02925; Japanese Patent Application No. 3-293179; and the like can be used.

In order that the prepared ferroelectric liquid crystal mixture has a low local minimum value $V_{min}$, spontaneous polarization should be decreased to some extent. Considering this, the spontaneous polarization is preferably 10 nC/cm² or less. Considering the orientation property, the prepared ferroelectric liquid crystal mixture preferably exhibits a chiral nematic phase, a smectic A phase, and a chiral smectic C phase.

Comparative Examples 1 to 4

Ferroelectric liquid crystal mixtures CFLC1 to CFLC4 each having a composition shown in Table 15 were prepared, using the liquid crystal mixture CLC1 having a composition shown in Table 14 and the compound shown in Table 1. The transition temperature of the ferroelectric liquid crystal mixtures CFLC1 to CFLC4 is shown in Table 16. The dielectric anisotropy of the ferroelectric liquid crystal mixtures CFLC1 to CFLC4 is in the vicinity of 0.

TABLE 14

$$K \xrightarrow{<RT} S_C \xrightarrow{51° C.} S_A \xrightarrow{63° C.} N \xrightarrow{69° C.} I$$

C₇H₁₅—[pyrimidine]—[phenyl]—OC₇H₁₅   5 wt %

C₇H₁₅—[pyrimidine]—[phenyl]—OC₈H₁₇   10 wt %

C₇H₁₅—[pyrimidine]—[phenyl]—OC₉H₁₉   15 wt %

C₈H₁₇—[pyrimidine]—[phenyl]—OC₈H₁₇   20 wt %

C₈H₁₇—[pyrimidine]—[phenyl]—OC₁₀H₂₁   30 wt %

C₉H₁₉—[pyrimidine]—[phenyl]—OC₆H₁₃   20 wt %

TABLE 15

| CFLC1 | | CFLC2 | | CFLC3 | | CFLC4 | |
|---|---|---|---|---|---|---|---|
| CLC1 | 98.0% | CLC1 | 95.0% | CLC1 | 90.0% | CLC1 | 98.0% |
| KLC372SA | 2.0% | KLC372SA | 5.0% | KLC372SA | 10.0% | KLC375SB | 2.0% |

TABLE 16

| | K | | $S_C^*$ | | $S_A$ | | N* | | I |
|---|---|---|---|---|---|---|---|---|---|
| CFLC1 | . | <RT | . | 53 | . | 63 | . | 69 | . |
| CFLC2 | . | <RT | . | 53 | . | 62 | . | 69 | . |
| CFLC3 | . | <RT | . | 53 | . | 59 | . | 68 | . |
| CFLC4 | . | <RT | . | 44 | . | 62 | . | 67 | . |

An ITO film and an SiO₂ film were formed in this order on two glass substrates, respectively. Then, a polyimide film was formed on the respective SiO₂ films. The polyimide films were rubbed to obtain alignment films. The two substrates having the alignment films were attached to each other so that the respective rubbing directions were identical and the cell gap was 2 μm. Thus, four pairs of liquid crystal cells were obtained. CFLC1 to CFLC4 were injected into the respective cells. After injection, each cell was heated to a temperature at which the liquid crystal mixture was changed to an isotropic phase. Thereafter, each cell was cooled to room temperature, whereby ferroelectric liquid crystal devices having satisfactory orientation were obtained.

Each of the ferroelectric liquid crystal devices thus obtained was placed between two polarizers orthogonal to each other. Each device was evaluated for the relation between the response time and an S93468 applied voltage. Under the condition that the temperature of the device was set at 25° C., various voltages with a rectangular waveform were applied to the cell. Time required for the relative transmittance to change from 0% to 50%, 0% to 90%, and 10% to 90% was measured.

Figure 16:
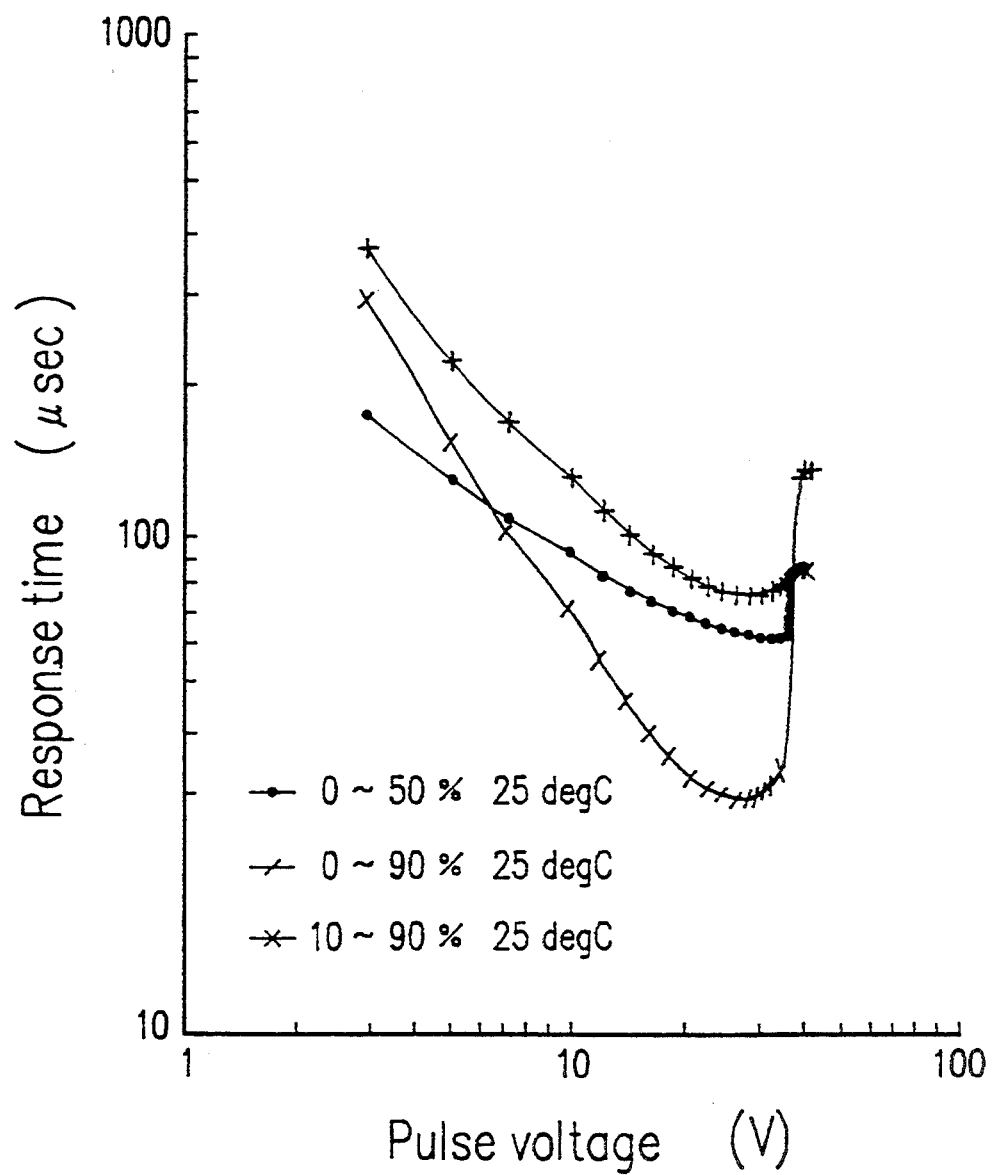
FIG. 16 is a graph showing the relationship between response time and a pulse voltage of a ferroelectric liquid crystal device of a comparative example.
Figure 17:
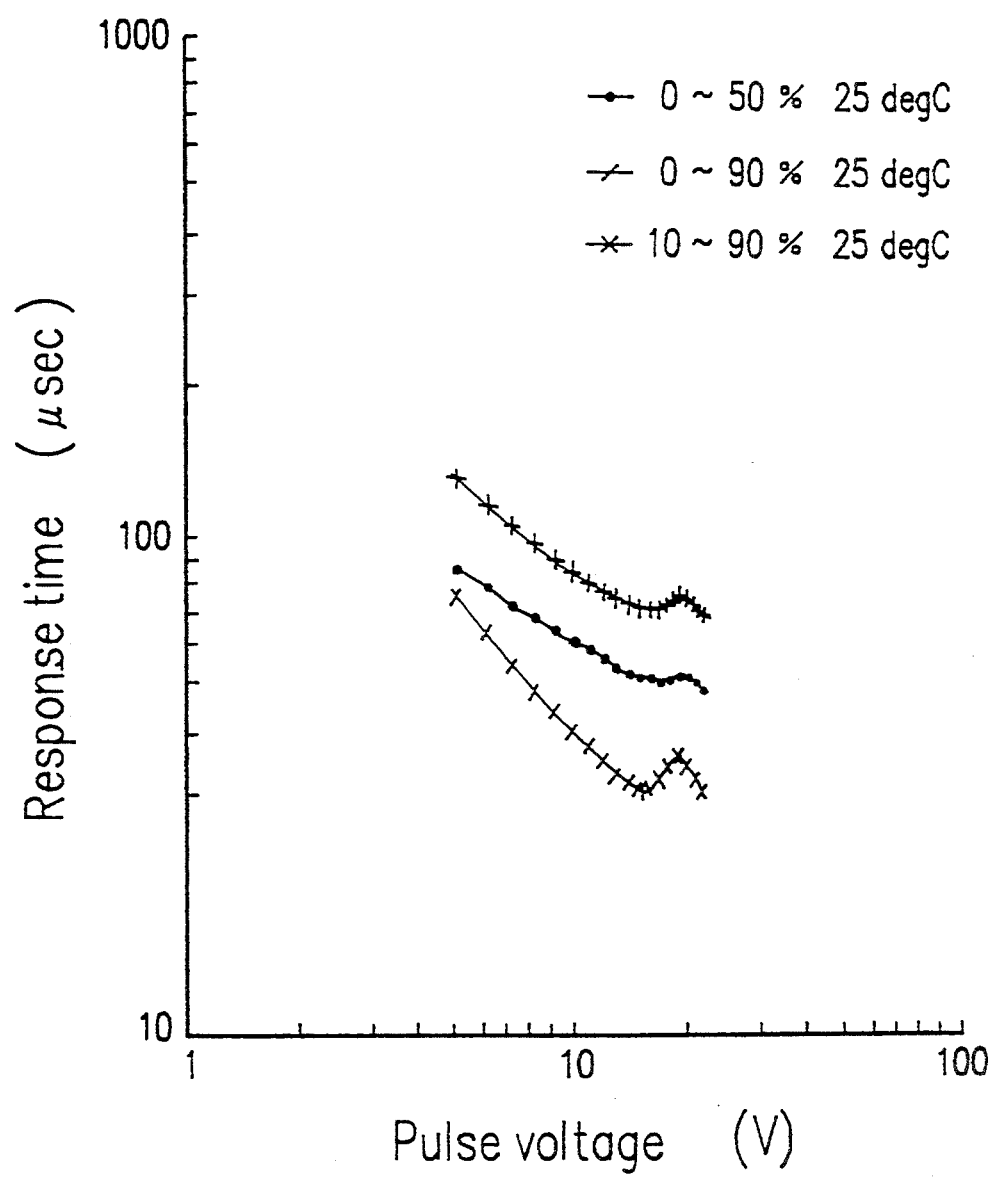
FIG. 17 is a graph showing the relationship between response time and a pulse voltage of a ferroelectric liquid crystal device of another comparative example.
Figure 18:
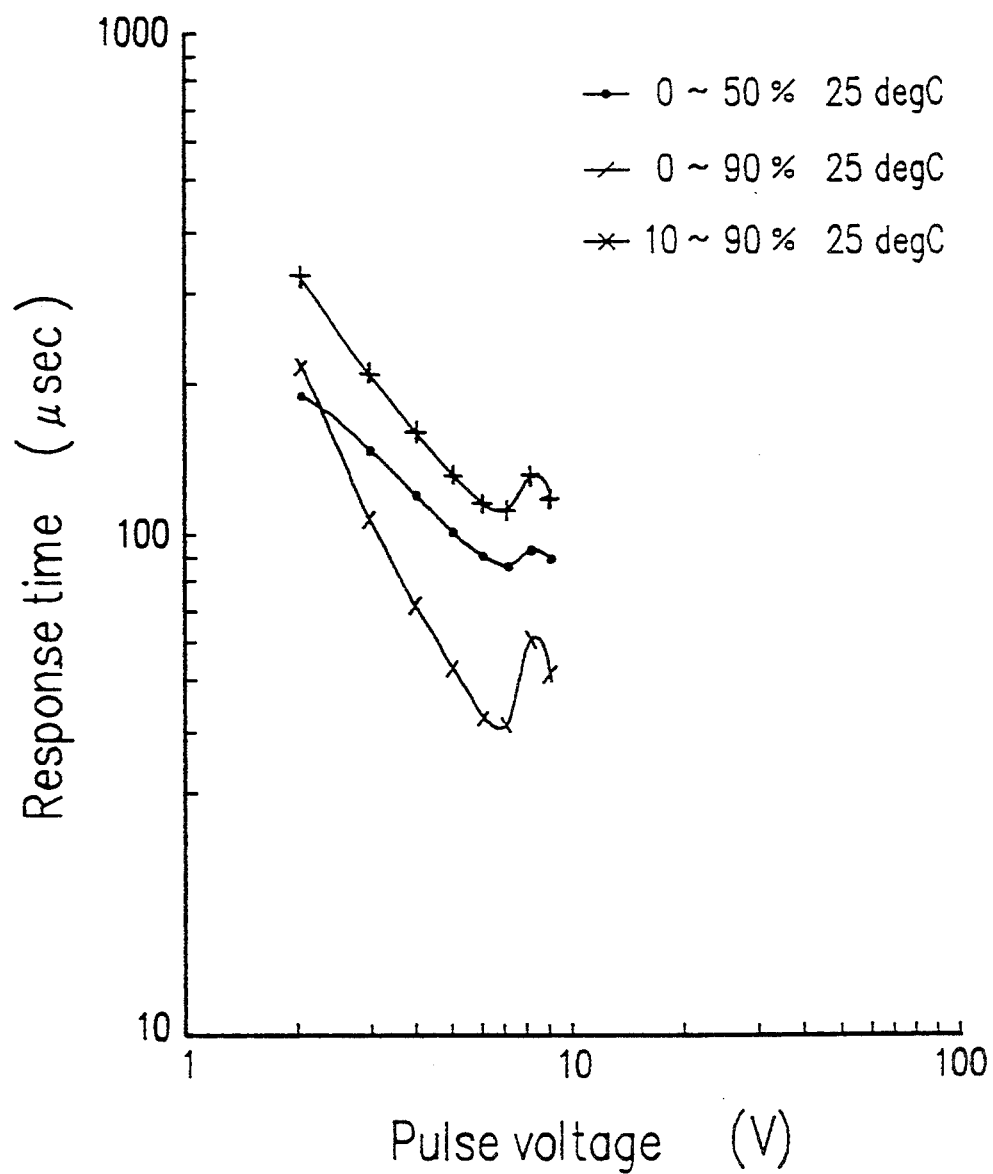
FIG. 18 is a graph showing the relationship between response time and a pulse voltage of a ferroelectric liquid crystal device of still another comparative example.

The results obtained with respect to the ferroelectric liquid crystal devices using CFLC1 to CFLC3 are respectively shown in FIGS. 16, 17, and 18. In the graphs, $V_{min}$ is recognized. However, the observation of the orientation of liquid crystal molecules in these liquid crystal devices by a microscope revealed that when a voltage of apparent $V_{min}$ or more in FIG. 16 was applied, the orientation of the liquid crystal molecules was changed. It is considered that the change in orientation of the liquid crystal molecules caused the apparent $V_{min}$.

Figure 19:
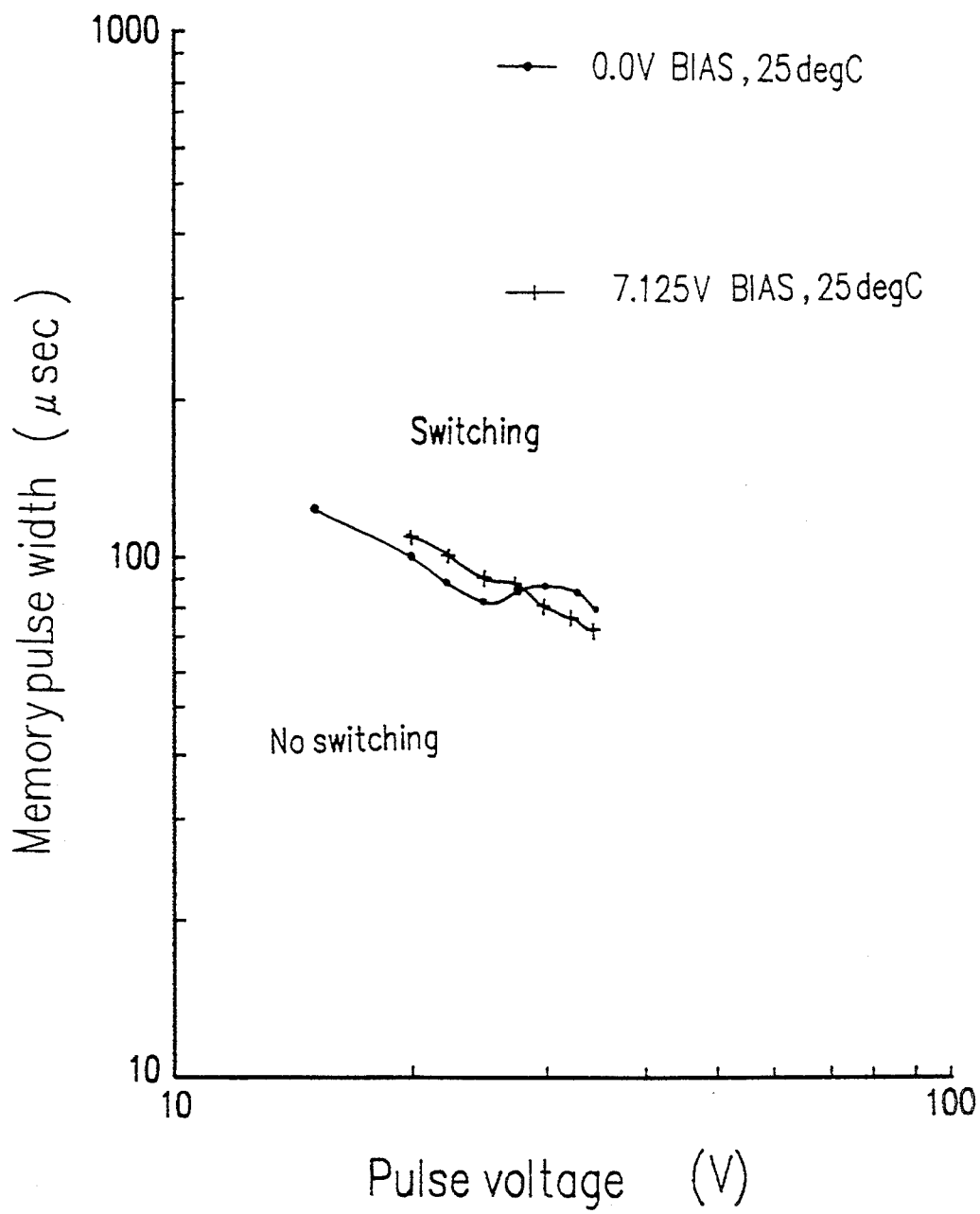
FIG. 19 is a graph showing a τ-V characteristic of a ferroelectric liquid crystal device of a comparative example.
Figure 20:
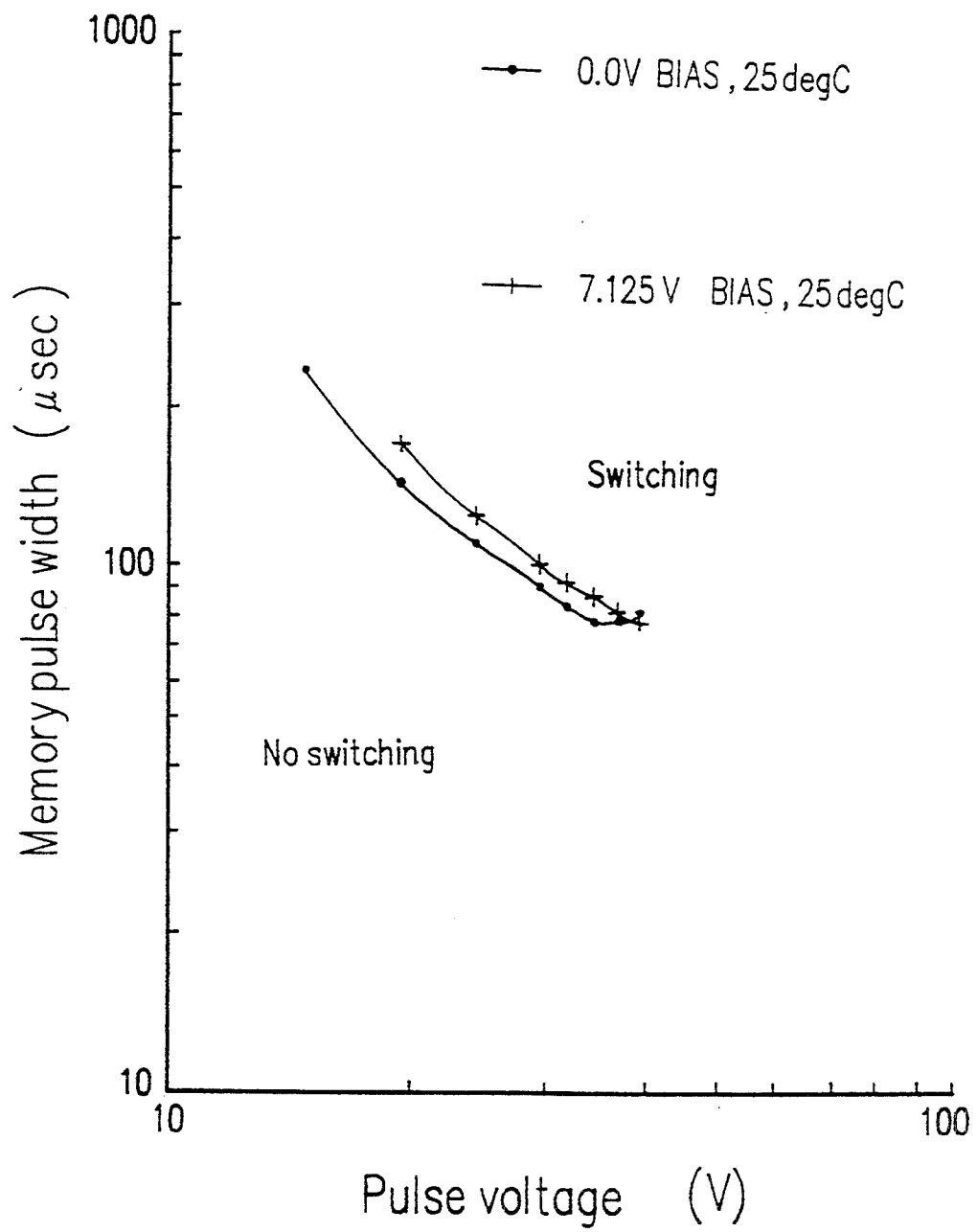
FIG. 20 is a graph showing a τ-V characteristic of a ferroelectric liquid crystal device of another comparative example.

Next, each device was evaluated for the relation ($\tau - V$ characteristic) between the pulse width required for memory (time) and a voltage value. The results for CFLC1 and CFLC4 are shown in FIGS. 19 and 20, respectively. In the $\tau - V$ characteristic, $V_{min}$ is not recognized.

These devices were driven using driving waveforms shown in FIGS. 2, 7, and 15. No satisfactory driving conditions were found. When a non-rewrite pulse having the same width as that of a rewrite pulse suitable for obtaining satisfactory switching was applied, rewrite occurred.

As described above, in the ferroelectric liquid crystal mixture having dielectric anisotropy in the vicinity of 0, the $\tau - V_{min}$ characteristic cannot be obtained and satisfactory driving cannot be conducted.

It is preferred that the ferroelectric liquid crystal mixture of the present invention has spontaneous polarization of 10 to 0.5 nC/cm$^2$.

As is understood from the above-mentioned examples, the ferroelectric liquid crystal device using the ferroelectric liquid crystal mixture of the present invention has a satisfactory orientation property, a high contrast, and a large capacity at a low driving voltage.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A ferroelectric liquid crystal mixture including at least one chiral compound, having negative dielectric anisotropy and exhibiting a chiral smectic C phase, containing at least one compound selected from the group consisting of a compound represented by the following general Formula I:

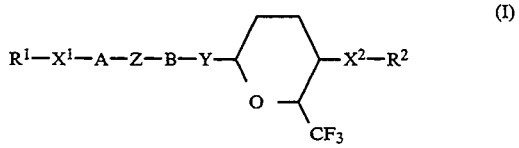

where $R^1$ and $R^2$ are the same or different straight-chain or branched chain alkyl groups having 1 to 15 carbon atoms; $X^1$ is a single bond, —O—, —COO—, or —OCO—; $X^2$ is —O— or —OCO—; Y is —COO— or —CH$_2$O; A and B are independently a group including a six membered ring which can be substituted by halogen, a cyano group, a lower alkoxy group, or a fluorine-containing alkyl group; and Z is a single bond, -COO-, or —OCO—, and a compound represented by the following general Formula II:

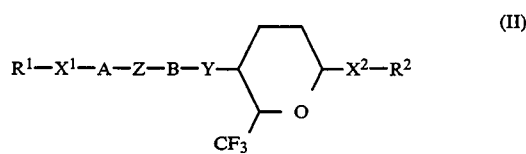

where $R^1$ and $R^2$ are the same or different straight-chain or branched chain alkyl groups having 1 to 15 carbon atoms; $X^1$ is a single bond, —O—, —COO—, or —OCO—; $X^2$ is —O— or —OCO—; Y is —COO— or —CH$_2$O; A and B are independently a group including a six membered ring which can be substituted by halogen, a cyano group, a lower alkoxy group, or a fluorine-containing alkyl group; and Z is a single bond, —COO—, or —OCO—.

2. A ferroelectric liquid crystal mixture according to claim 1, wherein the compound represented by Formula I and the compound represented by Formula II are chiral compounds.

3. A ferroelectric liquid crystal mixture according to claim 2, containing the chiral compound represented by Formula I and the chiral compound represented by Formula II.

4. A ferroelectric liquid crystal mixture according to claim 1, exhibiting a chiral smectic C phase, a smectic A phase, and a chiral nematic phase.

5. A ferroelectric liquid crystal mixture according to claim 1, containing a compound represented by the following general Formula III:

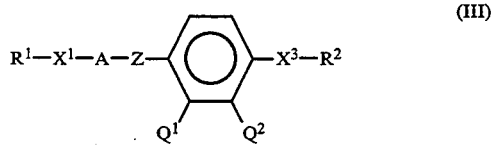

where $R^1$ and $R^2$ are the same or different straight-chain or branched chain alkyl groups having 1 to 15 carbon atoms; $X^1$ is a single bond, —O—, —COO—, or —OCO—; $X^3$ is a single bond, —O—, —COO—, or —OCO—; A is a group including a six membered ring which can be substituted by halogen, a cyano group, a lower alkoxy group, or a fluorine-containing alkyl group; Z is a single bond, —COO—, or —OCO—; $Q^1$ and $Q^2$ are H, F, CN, or CF$_3$, and at least one of $Q^1$ and $Q^2$ is not H.

6. A ferroelectric liquid crystal mixture according to claim 2, wherein $R^1$ and $R^2$ are independently a straight chain or branched chain alkyl group having 5 to 8 carbon atoms, A and B are independently a phenylene group which can be substituted by halogen, a cyano group, a lower alkoxy group, or a fluorine-containing alkyl group, and Z is a single bond in Formula I or II.

7. A ferroelectric liquid crystal mixture according to claim 6, wherein the chiral compound is selected from the group consisting of a compound represented by the following Formulae and enantiomers thereof

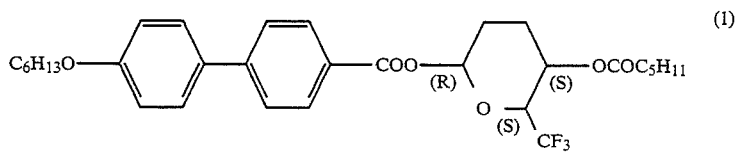
(1)

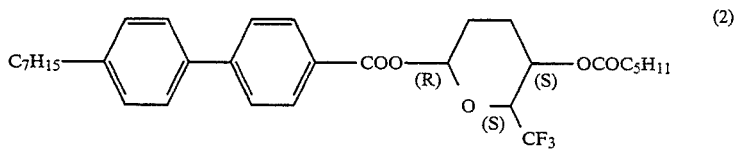
(2)

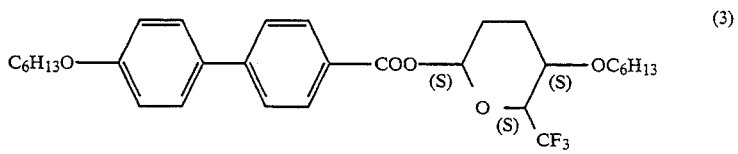
(3)

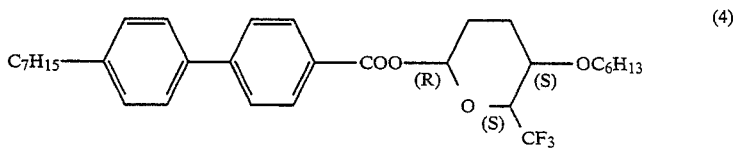
(4)

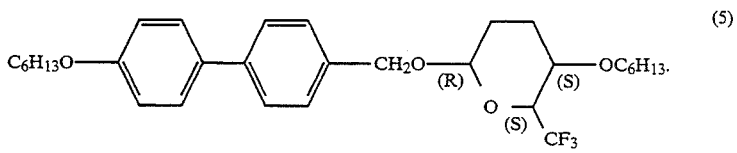
(5)

8. A ferroelectric liquid crystal mixture according to claim 7, wherein the chiral compound is selected from the group consisting of a compound represented by the following Formulae and enantiomers thereof

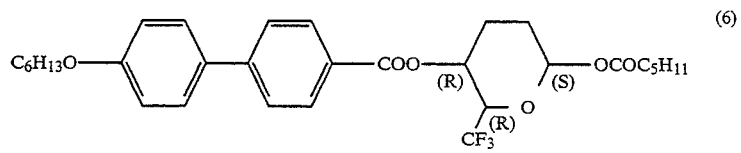
(6)

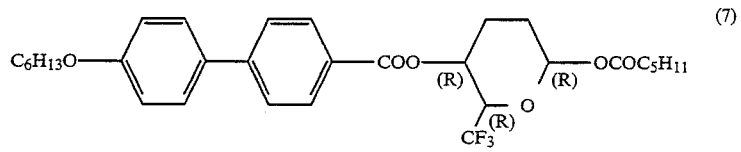
(7)

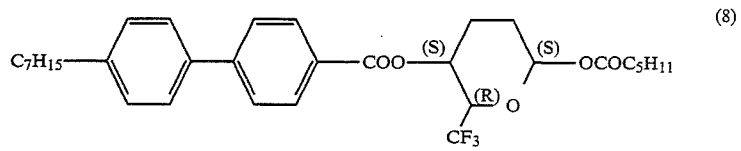
(8)

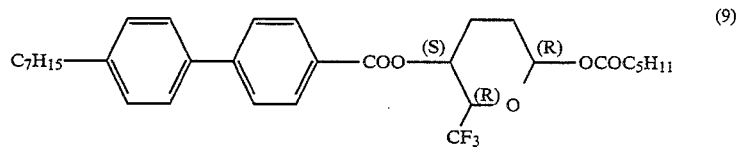
(9)

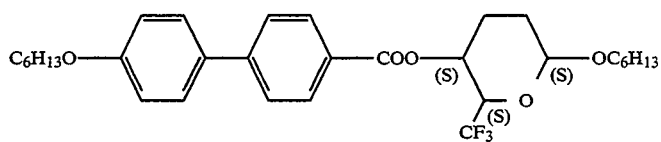
(10)

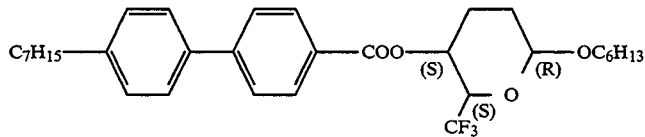
(11)

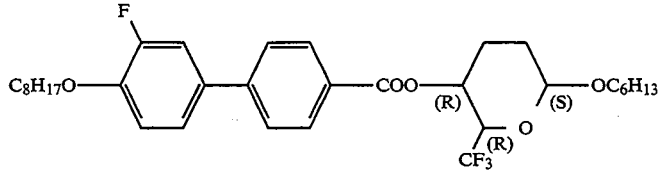
(12)

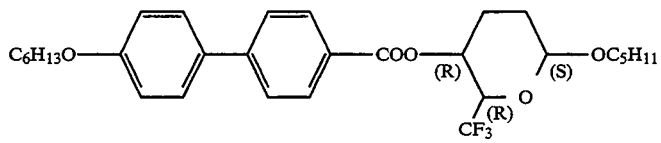
(13)

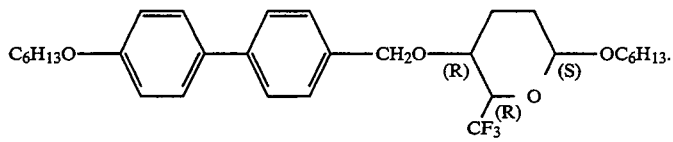
(14)

9. A ferroelectric liquid crystal mixture according to claim 2, containing the compound represented by Formula I in an amount of 0.01 to 5 wt % based on the total amount of the ferroelectric liquid crystal mixture.

10. A ferroelectric liquid crystal mixture according to claim 2, containing the compound represented by Formula II in an amount of 0.01 to 5 wt % based on the total amount of the ferroelectric liquid crystal mixture.

11. A ferroelectric liquid crystal mixture according to claim 1, wherein the compound represented by Formula I and the compound represented by Formula II are achiral compounds, and the achiral compounds are contained in the ferroelectric liquid crystal mixture in an amount of 5 to 20 wt % based on the total amount of the ferroelectric liquid crystal mixture.

12. A liquid crystal device comprising a pair of facing substrates, liquid crystal sandwiched between the pair of substrates, means for aligning the liquid crystal, and means for applying a voltage to the liquid crystal, wherein the liquid crystal is made of a ferroelectric liquid crystal mixture having negative dielectric anisotropy and exhibiting a chiral smectic C phase containing a compound selected from the group consisting of the compound represented by the following Formula I:

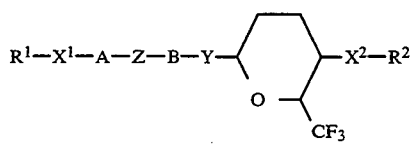
(I)

where $R^1$ and $R^2$ are the same or different straight-chain or branched chain alkyl groups having 1 to 15 carbon atoms; $X^1$ is a single bond, —O—, —COO—, or —OCO—; $X^2$ is —O— or —OCO—; Y is —COO— —CH$_2$O—; A and B are independently a group including a six membered ring which can be substituted by halogen, a cyano group, a lower alkoxy group, or a fluorine-containing alkyl group; and Z is a single bond, —COO—, or —OCO—, and a compound represented by the following general Formula II:

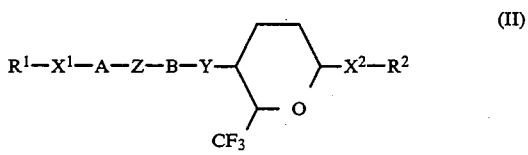
(II)

where $R^1$ and $R^2$ are the same or different straight-chain or branched chain alkyl groups having 1 to 15 carbon atoms; $X^1$ is a single bond, —O—, —COO—, —OCO—; $X^2$ is —O— or —OCO—; Y is —COO— or —CH$_2$O; A and B are independently a group including a six membered ring which can be substituted by halogen, a cyano group, a lower alkoxy group, or a fluorine-containing alkyl group; and Z is a single bond, —COO—, or —OCO—.

13. A liquid crystal device according to claim 12, wherein the compound represented by Formula I and the compound represented by Formula II are chiral compounds.

* * * * *